US007648995B2

(12) United States Patent
Neumeyer et al.

(10) Patent No.: US 7,648,995 B2
(45) Date of Patent: Jan. 19, 2010

(54) R(—)-11-HYDROXYAPORPHINE DERIVATIVES AND USES THEREOF

(75) Inventors: John L. Neumeyer, Wayland, MA (US); Ross J. Baldessarini, Newton, MA (US)

(73) Assignee: The McLean Hospital Corporation, Belmont, MA (US)

( * ) Notice: Subject to any disclaimer, the term of this patent is extended or adjusted under 35 U.S.C. 154(b) by 270 days.

(21) Appl. No.: 11/105,024

(22) Filed: Apr. 13, 2005

(65) Prior Publication Data

US 2006/0040900 A1  Feb. 23, 2006

Related U.S. Application Data

(60) Provisional application No. 60/562,156, filed on Apr. 13, 2004.

(51) Int. Cl.
*A61K 31/473* (2006.01)
*C07D 221/18* (2006.01)
(52) U.S. Cl. .......................... 514/284; 546/75
(58) Field of Classification Search ................. 514/284; 546/75
See application file for complete search history.

(56) References Cited

U.S. PATENT DOCUMENTS 4,687,773 A * 8/1987 Neumeyer et al. .......... 514/280
5,258,384 A   11/1993 Cannon et al.
5,744,476 A    4/1998 Locke et al.
5,994,363 A   11/1999 El-Rashidy et al.
6,313,134 B1  11/2001 Su et al.
7,057,044 B2   6/2006 Su et al.

FOREIGN PATENT DOCUMENTS

WO   WO 90/12574   * 11/1990

OTHER PUBLICATIONS

Ram, V. et al.: Synthesis of® -1,2,11-trihydroxy-,® -2,11-, and® -2,10-dihydroxyaporphines. J. heterocyc. Chem. vol. 28, pp. 1721-1724, 1991.*
Gao, Y. et al.: Synthesis and dopamine agonist and antagonist effects of ( R )-(–)-and (S)-(+)-11-hydroxy-N-n-propylnoraporphine. J. Med. Chem. vol. 31, pp. 1392-1396, 1988.*
Granchelli, F. et al.: Aporphines. 23. Normorphothebaine derivatives: Synthesis of an aporphine nitrogen mustard. J. Org. Chem. vol. 42, pp. 2014-2017, 1977.*
Baldessarini et al., "Receptor Affinities of Aporphine Enantiomers in Rat Brain Tissue," *Eur. J. Pharmacol.* 254:199-203 (1994).
Baldessarini et al., "Prolonged Apomorphine-Like Behavioural Effects of Apomorphine Esters," *Neuropharmacology* 15:471-478 (1976).
Baldessarini et al., "Prolonged D2 Antidopaminergic Activity of Alkylating and Nonalkylating Derivatives of Spiperone in Rat Brain," Mol. Pharmacol. 42:856-863 (1992).

Berenyi et al., "Synthesis of New N-Substituted N-Demethylaporphine Derivatives," *Acta Chim. Hung.* 120:201-205 (1985).
Berenyi et al., "Preparation of Demethoxyoripavine and Its Conversion into N-Substituted N-Demethylapomorphine Derivatives," Acta Chim. Hung. 113:51-60 (1983).
Berenyi et al., "A New Efficient Method for the Preparation of 2-Fluoro-N-propylnorapomorphine," *J. Chem. Soc. Perkin Trans.* I.:2693-2694 (1992).
Berenyi et al., "Rearrangement of Morphinandienes in Methanesulfonic Acid," *J. Chem. Perkin Trans.* 1:2137-2139 (1993).
Campbell et al., "Behavioral Effects of (–)10,11-Methylenedioxy-N-n-propylnoraporphine, An Orally Effective Long-Acting Agent Active at Central Dopamine Receptors, and Analogous Aporphines," *Neuropharmacology* 21:953-961 (1982).
Campbell et al., "Selective Antidopaminergic Effects of S(+)N-n-propylnoraporphines in Limbic Versus Extrapyramidal Sites in Rat Brain: Comparisons with Typical and Atypical Antipsychotic Agents" *Psychopharmacology* (Berl.) 103:323-329 (1991).
Cannon et al., "(R)-(–)-10-Methyl-11-hydroxyaporphine: a Highly Selective Serotonergic Agonist," *J. Med. Chem.* 31:313-318 (1988).
Granchelli et al., "Aporphines. 27. Mechanistic Aspects of the Rearrangement of Thebaine and Codeine Analogues in Methanesulfonic Acid. Improved Method for Synthesis of N-Alkylated Aporphines," *J. Org. Chem.* 45:2275-2282 (1980).
Hedberg et al., "(R)-11-Hydroxy- and (R)-11-Hydroxy-10-methylaporphine: Synthesis, Pharmacology, and Modeling of $D_{2A}$ and $5-HT_{1A}$ Receptor Interactions,"*J. Med. Chem.* 38:647-658 (1995).
Joyce, "Multiple Dopamine Receptors and Behavior," *Neurosci. Biobehav. Rev.* 7:227-256 (1983).
Kula et al., "[3H]β-CIT: A Radioligand for Dopamine Transporters in Rat Brain Tissue," *Eur. J. Pharmacol.* 385:291-294 (1999).
Kula et al., "RBI-257: A Highly Potent Dopamine $D_4$ Receptor-Selective Ligand," *Eur. J. Pharmacol* 331:333-336 (1997).
Makleit et al., "Conversions of Tosyl and Mesyl Derivatives of the morphine Group, XI," Acta Chim. Sci. Hung. 74:111-113(1972).
Martinez et al. "Clinical Experience with Apomorphine Hydrochloride: the First 107 Patients," *J. Urology* 170:2352-2355 (2003).
Neumeyer et al., "Therapeutic and Diagnostic Agents for Parkinson's Disease" Chapter 12, vol. 6, Abraham D (ed): Burger's Medicinal Chemistry and Drug Discovery, 6th Edition. New York, John Wiley & Sons, pp. 711-741 (2003).
Neumeyer and Baldessarini, "Apomorphine: New Uses for an Old Drug," *Pharmaceut. News* 4:12-16 (1997).
Neumeyer et al. "Aporphines, 36. Dopamine Receptor Interactions of Trihydroxyaporphines. Synthesis, Radioreceptor Binding, and Striatal Adenylate Cyclase Stimulation of 2,10,11-Trihydroxyaporphines in Comparison with Other Hydroxylated Aporphines," *J. Med. Chem* 24:1440-1445 (1981).
Neumeyer et al., "R and S Enantiomers of 11-Hydroxy- and 10,11-Dihydroxy-N-allylnoraporphine: Synthesis and Affinity for Dopamine Receptors in Rat Brain Tissue" *J. Med. Chem.* 34:24-28 (1991).

(Continued)

*Primary Examiner*—Charanjit S Aulakh
(74) *Attorney, Agent, or Firm*—Clark & Elbing LLP; Paul T. Clark

(57) ABSTRACT

The invention features derivatives of R(—)-11-hydroxyaporphines and methods of treating Parkinson's disease, sexual dysfunction, and depressive disorders therewith.

24 Claims, 1 Drawing Sheet

OTHER PUBLICATIONS

Neumeyer and Granchelli, "Aporphines. 11. Synthesis and Dopaminergic Activity of Monohydroxyaporphines. Total synthesis of (+,−)-11-Hydroxyaporphine, (+,−)-11-Hydroxynoraporphine, and (+,−)-11-Hydroxy-N-n-propylnoraporphine," *J. Med. Chem.* 17:1090-1095 (1974).

Ram and Neumeyer, "Aporphines. 42. Synthesis of (R)-(−)-11-Hydroxyaporphines from Morphine," *J. Org. Chem.* 47:4372-4374 (1982).

Rodenhuis, et al. "Dopamine $D_2$ activity of R-(−)-Apomorphine and Selected Analogs: a Microdialysis Study," *Eur. J. Pharmacol.* 387:39-45 (2000).

Schaus et al., "Aporphines as Antagonists of Dopamine D-1 Receptors," *J. Med. Chem.* 33:600-607 (1990).

Simon et al. "Synthesis of C-3 Halogene-Substituted Apocodeins and Apomorphines," *Synth Commun.* 21:2309-2316 (1991).

Sit, "Dopamine Agonists in the Treatment of Parkinson's Disease—Past, Present and Future," *Current Pharmaceutical Design* 6:1211-1248 (2000).

Ungerstedt, "Striatal Dopamine Release after Amphetamine or Nerve Degeneration Revealed by Rotational Behaviour," *Acta Physiol. Scand. Suppl.* 367:49-68 (1971).

Weiss and Daum, "Derivatives of Morphine. IV.[1] 14-Hydroxymorphine and 14-Hydroxydihydromorphine," *J. Med. Chem.* 39:123-125 (1965).

Zhang et al., "Nigrostriatal Dopaminergic Denervation Enhances Dopamine $D_4$ Receptor Binding in Rat Caudate-Putamen," *Pharmacol. Biochem. Behav.* 39:111-116 (2001).

Zhang et al., "Role of Dopamine D4 receptors in motor Hyperactivity Induced by Neonatal 6-hydroxydopamine lesions in rats," *Neurophyschopharmacology* 25:624-632 (2001).

Atkinson et al. "Derivatives of Apomorphine and of Other N-Substituted Norapomorphines," *J. Pharmacol. Sci.* 65:1682-1685 (1976).

Baldessarini et al. "Esters of Apomorphine and N,N-Dimethyldopamine as Agonists of Dopamine Receptors in the Rat Brain in Vivo," *Neuropharmacology* 14:725-731 (1975).

Borgman et al. "Diester Derivatives as Apomorphine Prodrugs," *J. Med. Chem.* 19:717-719 (1976).

Csutoras et al. "Synthesis and Neuropharmacological Evaluation of R(−)-N-alkyl-11-hydroxynoraporphines and Their Esters," *Bioinorg. Med. Chem.* 12:3553-3559 (2004).

Gao et al. "Synthesis and Dopamine Agonist and Antagonist Effects of (R)-(−)-and (S)-(+)-11-Hydroxy-N-n-propylnoraporphine," *J. Med. Chem.* 31:1392-1396 (1988).

Granchelli et al. "Aporphines. 23. Normorphothebaine Derivatives: Synthesis of an Aporphine Nitrogen Mustard," *J. Org. Chem.* 42:2014-2017 (1977).

Ram and Neumeyer, "Synthesis of (R)-1,2,11-Trihydroxy-, (R)-2,11-, and (R)-2,10-Dihydroxyaporphines—Non Naturally Occurring Aporphine Alkaloids from Pukateine and Thebaine," *J. Heterocyclic Chem.* 28:1721-1724.

Scatton and Worms, "Subsensitivity of Striatel and Mesolimbic Dopamine Target Cells after Repeated Treatment with Apomorphine Dipivaloyl Ester," *Naunym-Schmiedeberg's Arch. Pharmacol.* 303:271-278(1978).

Scatton and Worms, "Tolerance to Increases in Striatel Acetylcholine Concentrations after Repeated Administration of Apomorphine Dipivaloyl Ester," *J. Pharm. Pharmacol.* 31:861-863 (1979).

Worms and Scatton, "Tolerance to Stereotyped Behavior and to Decrease in Striatel Homovanillic Acid Levels after Repeated Treatment with Apomorphine Dipivaloyl Ester," *Eur. J. Pharmacol.* 45:395-396 (1977).

Yu, "Thaliporphine Selectively Inhibits Expression of the Inducible, but not the Constitutive, Nitric Oxide Synthase," *Biochem. J.* 303:289-294 (1994).

Zijlstra et al. "Behavior of Reaction Mixtures under Microwave Conditions: Use of Sodium Salts in Microwave-Induced N-[$^{18}$F]Fluoroalkylations of Aporphine and Tetralin Derivatives," *J. Org. Chem.* 58:1643-1645 (1993).

Campbell et al., "R(−) and S(+) Stereoisomers of 11-Hydroxy- and 11-Methoxy-N-n-Propylnoraporphine: Central Dopaminergic Behavioral Activity in the Rat." *Neuropharmacology.* 29(6):527-536. (1990).

Neumeyer et al., "Aporphines 65: Chemical, Microbial Synthesis and Characterization by Gas Chromatography/Mass Spectrometry of (R)-(−)-10-Hydroxy 11-Methoxy-N-n-Propylnoraporphine, a Potential Metabolite of N-n-Propylnorapomorphine." *Biomed. Environ. Mass Spectrom.* 13(5):223-229 (1986).

* cited by examiner

Agents were administered orally at 20 μmol/kg. Rats with unilateral lesions of dopamine projections to forebrain induced by the neurotoxin 6-hydroxydopamine were scored for the number of rotations contralateral to the lesioned side per 5 min. Data are rates of rotation ± SEM (N=5).

R(—)-11-HYDROXYAPORPHINE DERIVATIVES AND USES THEREOF

CROSS-REFERENCE TO RELATED APPLICATIONS

The application claims benefit of U.S. Provisional Application No. 60/562,156, filed Apr. 13, 2004, which is incorporated herein by reference.

BACKGROUND OF THE INVENTION

The invention relates to the treatment of Parkinson's disease, sexual dysfunction, and depressive disorders.

Parkinson's disease is a progressive neurodegenerative disorder of the basal ganglia of the brain, which most often becomes apparent after the age of 55. It is a prevalent and prototypic hypokinetic disorder, with akinesia, bradykinesia, rigidity and tremor as the most prominent features. The neurological and psychiatric symptoms, including depression and psychosis, with late dementia, usually worsen with time. The neuropathology of Parkinson's disease reveals a striking and selective loss of the dopaminergic neurons of the nigrostriatal pathway of the brain.

As Parkinson's disease is associated with a loss of the neurotransmitter dopamine, it is commonly treated with drugs which replace or mimic the actions of dopamine. Since dopamine itself cannot pass the blood-brain diffusion barrier, the most commonly used therapy is levodopa (L-DOPA), the immediate precursor of dopamine which is readily decarboxylated by remaining dopaminergic neurons and other amine-producing neurons. A complication of long-term treatment with L-DOPA is the development of rapid fluctuations in clinical state such that the patient changes, often abruptly, between mobility and immobility; this phenomenon is known as the 'on-off' effect.

An alternative approach to treatment with L-DOPA is the use of drugs (dopamine agonists and partial-agonists) that mimic the actions of dopamine. Treatment with dopamine receptor agonists has some advantages over treatment with L-DOPA. Unlike L-DOPA, dopamine agonists are effective in patients with advanced stages of Parkinson's disease because their action at postsynaptic receptors is unaffected by the lack of dopamine producing nerve cells that decarboxylate L-DOPA to produce dopamine locally, whereas the denervated dopamine receptors are supersensitive to agonists. Furthermore, there is an increasing interest in the potential of dopamine receptor agonists to provide a neuroprotective effect. Theoretically, such a protective effect might result from (i) a decreased need for the use of L-DOPA, a substance that may cause oxidative stress and perhaps even contribute to further damage of dopamine neurons, (ii) stimulation of dopamine autoreceptors resulting in decreased dopamine synthesis, release, and turnover, resulting in reduced metabolism of dopamine to reactive oxygen species, and (iii) by direct anti-oxidant effects.

R(—)-Apomorphine is a directly acting dopamine agonist at both $D_1$ and $D_2$ receptors, and dopamine autoreceptors, without opiate-like or addictive properties. Apomorphine therapy has led to sustained improvements in Parkinson's disease patients with refractory motor oscillations (on-off phenomena). However, it is difficult to administer owing to its poor bioavailability and extensive first-pass metabolism to inactive metabolites. Therefore, apomorphine is usually administered either by intermittent subcutaneous injection or continuous subcutaneous infusion. Following a single dose, apomorphine has an onset of action of 5-15 minutes, and its effects last for 40-60 minutes.

Direct dopamine agonists, including R(—)-apomorphine, are also effective in the treatment of a number of forms of sexual dysfunction, primarily, but not limited to erectile dysfunction. See Martinez et al., *J. Urology* 170:2352 (2003).

New compounds that overcome the practical problems associated with apomorphine therapy, particularly its lack of oral bioavailability and short half-life, are needed for the treatment of diseases, such as Parkinson's disease and erectile dysfunction.

SUMMARY OF THE INVENTION

The invention is based on the discovery of R(—)-11-hydroxyaporphine derivatives that have enhanced bioavailability and extended in vivo half lives in comparison to apomorphine. The compounds are useful for the treatment of diseases, such as Parkinson's disease, sexual dysfunction, and depressive disorders.

In a first aspect, the invention features a compound of formula I or a pharmaceutically acceptable salt or solvate thereof.

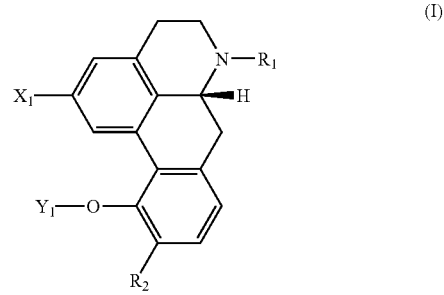

(I)

In formula I, $Y_1$ is C(O)—$R_3$, C(O)—O—$R_3$, C(O)—$NR_3R_4$, P(O)(OH)—O—$R_3$, C(S)—$R_3$, C(S)—O—$R_3$, C(S)—$NR_3R_4$, or fatty acid acyl; $X_1$ is H, F, Cl, Br, I, OH, OCH$_3$, or OC(O)—$R_5$; $R_1$ is H, $C_{1-4}$ alkyl, $C_{2-4}$ alkenyl, or $C_{2-4}$ alkynyl; $R_2$ is H, CH$_3$, or OCH$_3$; each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom; and $R_5$ is $C_{1-4}$ alkyl, $C_{2-4}$ alkenyl, or $C_{2-4}$ alkynyl. Desirably, $R_1$ is H, CH$_3$, CH$_2$CH$_3$, CH$_2$CH$_2$CH$_3$, CH$_2$CH=CH$_2$, or cyclopropylmethyl.

Compounds of formula I include those described by formulas II or a pharmaceutically acceptable salt or solvate thereof.

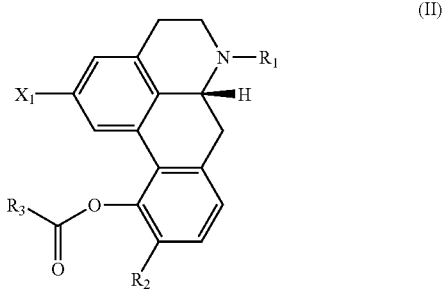

(II)

In formula II, $X_1$ is H, F, Cl, Br, I, OH, or OCH$_3$; $R_1$ is CH$_3$, CH$_2$CH$_3$, CH$_2$CH$_2$CH$_3$, CH$_2$CH=CH$_2$, or cyclopropylmethyl; $R_2$ is H, CH$_3$, or OCH$_3$; and $R_3$ is methyl, ethyl, n-propyl, isopropyl, cyclopropyl, cyclopropylmethyl, cyclopropylethyl, n-butyl, iso-butyl, sec-butyl, tert-butyl, vinyl, allyl, 2-cyclopropyl-1-ethenyl, 1-propenyl, 1-butenyl, 2-butenyl, 3-butenyl, 2-methyl-1-propenyl, 2-methyl-2-propenyl, ethynyl, 1-propynyl, 2-propynyl, 1-butynyl, 2-butynyl, or 3-butynyl.

Compounds of formula II include R(—)-11-O-acetyl-N-n-propyl-noraporphine, R(—)-11-O-propionyl-N-n-propyl-noraporphine, R(—)-11-O-isobutyryl-N-n-propyl-noraporphine, R(—)-11-O-butyryl-N-n-propyl-noraporphine, R(—)-11-O-isovaleryl-N-n-propyl-noraporphine, R(—)-11-O-valeryl-N-n-propyl-noraporphine, R(—)-10-O-methyl-11-O-acetyl-N-n-propyl-noraporphine, R(—)-10-methyl-11—O-propionyl-N-n-propyl-noraporphine, R(—)-10-methyl-11-O-isobutyryl-N-n-propyl-noraporphine, R(—)-10-methyl-11-O-butyryl-N-n-propyl-noraporphine, R(—)-10-methyl-11-O-isovaleryl-N-n-propyl-noraporphine, R(—)-10-methyl-11—O-valeryl-N-n-propyl-noraporphine, R(—)-10-methoxy-11-O-acetyl-N-n-propyl-noraporphine, R(—)-10-methoxy-11-O-propionyl-N-n-propyl-noraporphine, R(—)-10-methoxy-11-O-isobutyryl-N-n-propyl-noraporphine, R(—)-10-methoxy-11-O-butyryl-N-n-propyl-noraporphine, R(—)-10-methoxy-11-O-isovaleryl-N-n-propyl-noraporphine, R(—)-10-methoxy-11-O-valeryl-N-n-propyl-noraporphine, R(—)-2-fluoro-11-O-acetyl-N-n-propyl-noraporphine, R(—)-2-fluoro-11—O-propionyl-N-n-propyl-noraporphine, R(—)-2-fluoro-11-O-isobutyryl-N-n-propyl-noraporphine, R(—)-2-fluoro-11-O-butyryl-N-n-propyl-noraporphine, R(—)-2-fluoro-11-O-isovaleryl-N-n-propyl-noraporphine, and R(—)-2-fluoro-11-O-valeryl-N-n-propyl-noraporphine.

Compounds of formula I include those described by formulas III or a pharmaceutically acceptable salt or solvate thereof.

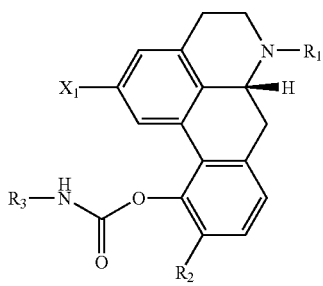

(III)

In formula III, $X_1$ is H, F, Cl, Br, I, OH, or $OCH_3$; $R_1$ is $CH_3$, $CH_2CH_3$, $CH_2CH_2CH_3$, $CH_2CH_2=CH_2$, or cyclopropylmethyl; $R_2$ is H, $CH_3$, or $OCH_3$; and $R_3$ is H, methyl, ethyl, n-propyl, isopropyl, cyclopropyl, cyclopropylmethyl, cyclopropylethyl, n-butyl, iso-butyl, sec-butyl, tert-butyl, vinyl, allyl, 2-cyclopropyl-1-ethenyl, 1-propenyl, 1-butenyl, 2-butenyl, 3-butenyl, 2-methyl-1-propenyl, 2-methyl-2-propenyl, ethynyl, 1-propynyl, 2-propynyl, 1-butynyl, 2-butynyl, or 3-butynyl.

Compounds of formula III include R(—)-11-O-methylcarbamoyl-N-n-propyl-noraporphine, R(—)-11-O-ethylcarbamoyl-N-n-propyl-noraporphine, R(—)-11—O-isopropyl-carbamoyl-N-n-propyl-noraporphine, R(—)-11-O-n-propylcarbamoyl-N-n-propyl-noraporphine, R(—)-11-O-isobutylcarbamoyl-N-n-propyl-noraporphine, R(—)-11-O-n-butylcarbamoyl-N-n-propyl-noraporphine, R(—)-10-methyl-11-O-methylcarbamoyl-N-n-propyl-noraporphine, R(—)-10-methyl-11—O-ethylcarbamoyl-N-n-propyl-noraporphine, R(—)-10-methyl-11-O-isopropylcarbamoyl-N-n-propyl-noraporphine, R(—)-10-methyl-11-O-n-propyl-carbamoyl-N-n-propyl-noraporphine, R(—)-10-methyl-11-O-isobutylcarbamoyl-N-n-propyl-noraporphine, R(—)-10-methyl-11-O-n-butylcarbamoyl-N-n-propyl-noraporphine, R(—)-10-methoxy-11-O-methylcarbamoyl-N-n-propyl-noraporphine, R(—)-10-methoxy-11-O-ethylcarbamoyl-N-n-propyl-noraporphine, R(—)-10-methoxy-11-O-isopropylcarbamoyl-N-n-propyl-noraporphine, R(—)-10-methoxy-11-O-n-propylcarbamoyl-N-n-propyl-noraporphine, R(—)-10-methoxy-11-O-isobutylcarbamoyl-N-n-propyl-noraporphine, R(—)-10-methoxy-11-O-n-butylcarbamoyl-N-n-propyl-noraporphine, R(—)-2-fluoro-11-O-methylcarbamoyl-N-n-propyl-noraporphine, R(—)-2-fluoro-11-O-ethylcarbamoyl-N-n-propyl-noraporphine, R(—)-2-fluoro-11-O-isopropylcarbamoyl-N-n-propyl-noraporphine, R(—)-2-fluoro-11-O-n-propylcarbamoyl-N-n-propyl-noraporphine, R(—)-2-fluoro-11—O-isobutylcarbamoyl-N-n-propyl-noraporphine, and R(—)-2-fluoro-11-O-n-butylcarbamoyl-N-n-propyl-noraporphine.

The invention also features compound of formula IV or a pharmaceutically acceptable salt or solvate thereof.

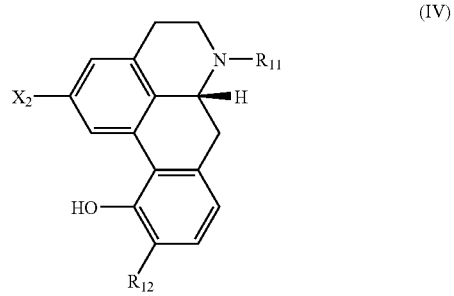

(IV)

In formula IV, $X_2$ is F, Cl, Br, I, OH, $OCH_3$, or OC(O)—$R_{13}$; $R_{11}$ is H, $C_{1-4}$ alkyl, $C_{2-4}$ alkenyl, or $C_{2-4}$ alkynyl; $R_{12}$ is H, $CH_3$, or $OCH_3$; and $R_{13}$ is $C_{1-4}$ alkyl, $C_{2-4}$ alkenyl, or $C_{2-4}$ alkynyl.

The invention also features a pharmaceutical composition comprising a compound of the invention together with a pharmaceutically acceptable excipient.

The invention features a method for treating Parkinson's disease, sexual dysfunction, or depressive disorders in a mammal, e.g., a human patient, by administering an effective amount of a compound of the invention. These compounds are particularly useful for treating depressive disorders, such as major depression, dysthymia, bipolar disorder (manic depression), and post traumatic stress disorder.

The compounds of the invention can be administered systemically, including, for example, by intravenous, intramuscular, or subcutaneous injection, orally, by inhalation, or by topical or transdermal application. Alternatively, the compounds can be centrally administered using, for example, by an intrathecal, intracerebroventricular, or intraparenchemal injection. Desirably, the compounds are administered orally.

For any of the above methods, the method optionally includes the step of administering an effective amount of an anti-emetic agent. An effective amount is an amount that reduces or prevents emesis and/or nausea in the mammal. Anti-emetic agents which can be used in the methods of the invention include, without limitation, nicotine, lobeline sulfate, pipamazine, oxypendyl hydrochloride, ondansetron, buclizine hydrochloride, cyclizine hydrochloride, dimenhydrinate, scopolamine, metopimazine, benzauinamine hydrochloride and diphenidol hydrochloride.

The methods and compositions described herein can also be used to generate information useful, for example, for increasing investment in a company or increasing consumer demand for the methods and/or compositions.

The invention therefore features a method of increasing consumer demand for a pharmaceutical composition or therapeutic regimen described herein. The method includes the step of disseminating information about the pharmaceutical composition or therapeutic regimen.

The invention further features a method of increasing investment in a company seeking governmental approval for the sale of a pharmaceutical composition or therapeutic regimen described herein. The method includes the steps of i) disseminating information about the pharmaceutical composition or therapeutic regimen, and ii) disseminating information about the intent of the company to market the pharmaceutical composition or therapeutic regimen.

Consumer demand for a pharmaceutical composition described herein, optionally with instructions to administer the pharmaceutical composition using a regimen described herein, can be increased by disseminating information about the utility, efficacy, or safety of the pharmaceutical composition or therapeutic regimen. Consumers include health maintenance organizations, hospitals, doctors, and patients. Typically, the information will be disseminated prior to a governmental approval for the sale of a composition or therapeutic regimen of the invention.

A company planning to sell a pharmaceutical composition described herein, optionally with instructions to administer the pharmaceutical composition using a regimen described herein, can increase investment therein by disseminating information about the company's intention to seek governmental approval for the sale of and disseminating information about the pharmaceutical composition or therapeutic regimen. For example, the company can increase investment by disseminating information about in vivo studies conducted, or planned, by the company, including, without limitation, information about the toxicity, efficacy, or dosing requirements of a pharmaceutical composition or therapeutic regimen of the invention. The company can also increase investment by disseminating information about the projected date of governmental approval of a pharmaceutical composition or therapeutic regimen of the invention.

Information can be disseminated in any of a variety of ways, including, without limitation, by press release, public presentation (e.g., an oral or poster presentation at a trade show or convention), on-line posting at a web site, and mailing. Information about the pharmaceutical composition or therapeutic regimen can include, without limitation, a structure, diagram, figure, chemical name, common name, tradename, formula, reference label, or any other identifier that conveys the identity of the pharmaceutical composition or therapeutic regimen of the invention to a person.

By "in vivo studies" is meant any study in which a pharmaceutical composition or therapeutic regimen of the invention is administered to a mammal, including, without limitation, non-clinical studies, e.g., to collect data concerning toxicity and efficacy, and clinical studies.

By "projected date of governmental approval" is meant any estimate of the date on which a company will receive approval from a governmental agency to sell, e.g., to patients, doctors, or hospitals, a pharmaceutical composition or therapeutic regimen of the invention. A governmental approval includes, for example, the approval of a drug application by the Food and Drug Administration, among others.

The term "administration" or "administering" refers to a method of giving a dosage of a pharmaceutical composition to a patient, where the method is, e.g., oral, topical, transdermal, by inhalation, intravenous, intraperitoneal, intracerebroventricular, intrathecal, or intramuscular. The preferred method of administration can vary depending on various factors, e.g., the components of the pharmaceutical composition, site of administration, and severity of the symptoms being treated.

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to ameliorate the disease and improve the patient's condition. Thus, in the claims and embodiments, treating is the administration to a mammal either for therapeutic or prophylactic purposes.

As used herein, "sexual dysfunction" refers to disorders of orgasm, response timing, ejaculation, nociception, congestive arousal and erection, vasculogenic impairment, or desire. In males, the form of sexual dysfunction is typically erectile dysfunction, the inability to achieve and sustain an erection sufficient for intercourse. Females also can have sexual dysfunctions of arousal and orgasm that increase with age and are associated with the presence of vascular risk factors and onset of menopause. Some of the vascular and muscular mechanisms that contribute to penile erection in the male are believed to involve similar vasculogenic factors in female genital responses. Female sexual dysfunction includes a failure to attain or maintain vaginal lubrication-swelling responses of sexual excitement until completion of the sexual activity.

By "depressive disorder" is meant any psychological or psychiatric disorder associated with symptoms of depressed mood. Treatable depressive disorders may be characterized by an inhibition or reduction of dopaminergic function in the nucleus accumbens, e.g., major depression, dysthymia, bipolar disorder (manic depressions, and post-traumatic stress disorder.

The compounds and formulas described herein include addition salts, solvates, and polymorphs, thereof.

In the generic descriptions of compounds of this invention, the number of atoms of a particular type in a substituent group is generally given as a range, e.g., an alkyl group containing from 1 to 4 carbon atoms or $C_{1-4}$alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups.

By "$C_{1-4}$ alkyl" is meant a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups. $C_{1-4}$ alkyls include, without limitation, methyl, ethyl, n-propyl, isopropyl, cyclopropyl, cyclopropylmethyl, n-butyl, iso-butyl, sec-butyl, tert-butyl, and cyclobutyl.

By "$C_{1-12}$ alkyl" is meant a branched or unbranched hydrocarbon group having from 1 to 12 carbon atoms. A $C_{1-12}$ alkyl may be substituted or unsubstituted, may optionally include monocyclic or polycyclic rings, and includes the $C_{1-4}$alkyls above.

By "$C_{2-4}$ alkenyl" is meant a branched or unbranched hydrocarbon group containing one or more double bonds and having from 2 to 4 carbon atoms. A $C_{2-4}$ alkenyl may optionally include monocyclic or polycyclic rings, in which each ring desirably has from three to six members. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

By "$C_{2-12}$ alkenyl" is meant a branched or unbranched hydrocarbon group containing one or more double bonds and having from 2 to 12 carbon atoms. A $C_{2-12}$ alkenyl may be substituted or unsubstituted, may optionally include monocyclic or polycyclic rings, and includes the $C_{2-4}$ alkenyls above.

By "$C_{2-4}$ alkynyl" is meant a branched or unbranched hydrocarbon group containing one or more triple bonds and having from 2 to 4 carbon atoms. A $C_{2-4}$ alkynyl may optionally include monocyclic, bicyclic, or tricyclic rings, in which each ring desirably has five or six members. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{2-12}$ alkynyl" is meant a branched or unbranched hydrocarbon group containing one or more triple bonds and having from 2 to 12 carbon atoms. A $C_{2-12}$ alkynyl may be substituted or unsubstituted, may optionally include monocyclic or polycyclic rings, and includes $C_{2-4}$ alkynyls above.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups. Examples of $C_{1-7}$ heteroalkyls include, without limitation, methoxymethyl and ethoxyethyl.

By "halide" is meant bromine, chlorine, iodine, or fluorine.

By "fluoroalkyl" is meant an alkyl group that is substituted with a fluorine atom.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-2}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

By "fatty acid acyl" is meant a chemical moiety with the formula R—C(O)—, wherein R is a partially-saturated straight chain or branched hydrocarbon group having between 12 and 26 carbon atoms. Fatty acid acyls are derived from fatty acids including, without limitation, those occurring naturally in the brain. For example, fatty acids having 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). The fatty acids can be substituted or unsubstituted. Exemplary substituents include hydroxyl, halide, methyl, ethyl, propyl, isopropyl, butyl, and pentyl groups. Desirably, the fatty acid acyl is 4, 7, 10, 13, 16, 19 docosahexanoyl.

The invention features derivatives of R(—)-1-hydroxyaporphines and their use for the treatment of diseases, such as Parkinson's disease, sexual dysfunction, and depressive disorders. The compounds have enhanced bioavailability and extended in vivo half lives in comparison to apomorphine. As a result, the compounds of the invention can be administered in a more convenient and less invasive manner than currently used for apomorphine therapy.

Other features and advantages of the invention will be apparent from the following Drawings, Detailed Description, and the claims.

DETAILED DESCRIPTION

Figure 1:
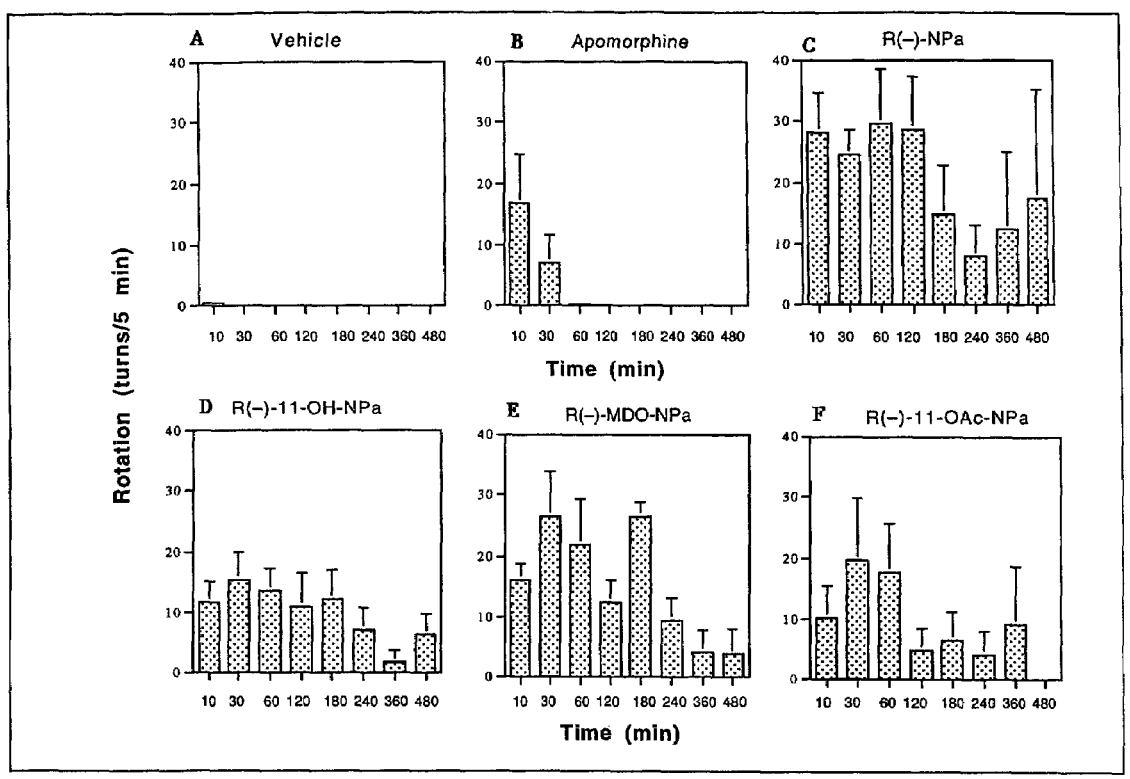
FIGS. 1A-1F show the effects of aporphines in the rat turning model (see Example 27). Agents were administered orally at 20 mmol/kg. Data are rates of rotation±SEM (N=5). R(—)—NPa is compound 2; R(—)-11-OH—NPa is compound 4, R(—)-11-OAc—NPa is compound 19, and R(—)-MDO-NPa is compound 11, 12-methylenedioxy-N-n-propylnoraporphine.

We have made compounds that are useful for the treatment of Parkinson's disease, sexual dysfunction, and depressive disorders.

The compounds are described by formulas I and IV below.

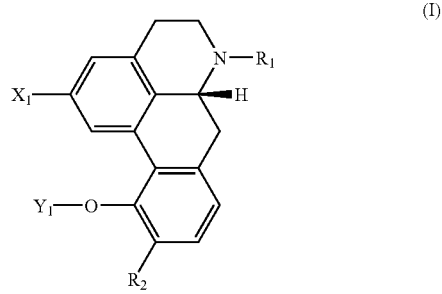

(I)

In formula I, $Y_1$ is C(O)—$R_3$, C(O)—O—$R_3$, C(O)—N$R_3R_4$, P(O)(OH)—O—$R_3$, C(S)—$R_3$, C(S)—O—$R_3$, C(S)—N$R_3R_4$, or fatty acid acyl; $X_1$ is H, F, Cl, Br, I, OH, $OCH_3$, or OC(O)—$R_5$; $R_1$ is H, $C_{1-4}$ alkyl, $C_{2-4}$ alkenyl, or $C_{2-4}$ alkynyl; $R_2$ is H, $CH_3$, or $OCH_3$; each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom; and $R_5$ is $C_{1-4}$ alkyl, $C_{2-4}$ alkenyl, or $C_{2-4}$ alkynyl.

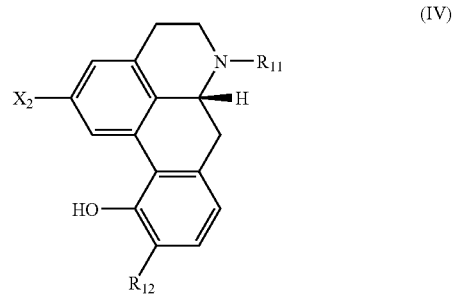

(IV)

In formula IV, $X_2$ is F, Cl, Br, I, OH, $OCH_3$, or OC(O)—$R_{13}$; $R_{11}$ is H, $C_{1-4}$ alkyl, $C_{2-4}$ alkenyl, or $C_{2-4}$ alkynyl; $R_{12}$ is H, $CH_3$, or $OCH_3$; and $R_{13}$ is $C_{1-4}$ alkyl, $C_{2-4}$ alkenyl, or $C_{2-4}$ alkynyl.

These compounds can be prepared as described in the Examples.

Assays

To determine their affinity for dopamine receptors, compounds of the invention can be characterized in radioligand receptor binding assays, as described in Example 24.

The in vivo potency and bioavailability of R(—)-11-hydroxyaporphine derivatives can be determined by administering the compound to an animal and monitoring the stimulation of motor activity as described in Example 25.

A symptom of clinical depression that can be modeled in rats is despair, a feeling of hopelessness. Symptoms of despair can be induced in rats using the forced swim test (FST), a highly validated model used to study antidepressant treatments. The efficacy of R(—)-11-hydroxyaporphine derivatives for the treatment of depressive disorders can be assessed using the forced swim test. The FST is a two day procedure in which rats swim under conditions in which escape is not possible. On the first day, the rats are forced to swim for 15 minutes. The rats initially search for an escape from the water, but eventually adopt a posture of immobility in which they make only the movements necessary to keep their heads above water. Upon re-testing one day later, latencies to become immobile (an indicator of how rapidly the rats "give up" in response to a familiar stressor) are decreased, which is inferred as despair. Standard antidepressants such as imipramine (IMI) and fluoxetine (FLX) extend latencies to become immobile. Drug efficacy in this animal model is predictive of antidepressant efficacy in humans. The FST has been described by Mague et al., *J. Pharmacol. Exp. Ther.* 305:323 (2003).

Therapy

Representative examples of diseases and conditions treatable using compounds of the present invention are as listed hereinabove, and include, but are not limited to, Parkinson's disease, sexual dysfunction, and depressive disorders, such as major depression and bipolar disorder.

Formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro A R., 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycolate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include calcium, zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) or median toxic dose ($TD_{50}$) to median effective dose ($ED_{50}$); (ii) a narrow absorption window in the gastrointestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticulate formulations, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Formulations for oral use also include rapidly disintegrating or dissolving dosage forms, also known as fast dissolve, fast or rapid melt, and quick disintegrating dosage forms. These dosage forms dissolve or disintegrate rapidly in the patient's mouth without chewing or the need for water within a short time frame. Because of their ease of administration, such compositions are particularly useful for the specific needs of pediatrics, geriatrics, and patients with dysphagia.

The formulations can be administered to patients in therapeutically effective amounts. For example, an amount is administered which prevents, reduces, or eliminates the symptoms of Parkinson's disease, sexual dysfunction, or depression, respectively. Typical dose ranges are from about 0.001 mg/kg to about 2 mg/kg of body-weight per day. Desirably, a dose of between 0.001 mg/kg and 1 mg/kg of body weight, or 0.005 mg/kg and 0.5 mg/kg of body weight, is administered. The exemplary dosage of drug to be administered is likely to depend on such variables as the type and extent of the condition, the overall health status of the particular patient, the formulation of the compound, and its route of administration. Standard clinical trials may be used to optimize the dose and dosing frequency for any particular compound.

The compounds of the invention may also be administered by a dose escalating method of acclimatization as described in U.S. Pat. No. 5,994,363 thereby ameliorating potential adverse effects. Furthermore, potential adverse effects can be ameliorated by administering R(—)-11-hydroxyaporphine compounds in combination with an anti-emetic agent, such as nicotine, lobeline sulfate, pipamazine, oxypendyl hydrochloride, ondansetron, buclizine hydrochloride, cyclizine hydrochloride, dimenhydrinate, scopolamine, metopimazine, benzauinamine hydrochloride or diphenidol hydrochloride.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Melting points were measured with a Thomas Hoover Capillary Melting Point Apparatus, and are uncorrected. $^1$H and $^{13}$C NMR spectra were obtained on Varian 300 spectrometer, chemical shifts are reported in ppm (δ) from internal TMS and coupling constants (J) are measured in Hz. Thin layer chromatography was performed on precoated Merck 5554 Silica gel 40 $F_{254}$ foils, the spots were visualized with Dragendorff's reagent. Mass spectra were measured with a Hewlett Packard 5.972 series GC-MS instrument.

R(—)-apomorphine 1 and R(—)—N-propylnorapomorphine 2 were synthesized by the procedure of Berenyi et al., Acta. Chim. Hung. 113:51 (1983), using the methanesulfonic acid catalyzed rearrangement of the appropriate morphinanedienes. Compounds of the invention can be prepared as shown in Scheme 1, below. R(—)-11-hydroxy-10-methoxy-aporphines and R(—)-11-hydroxy-10-methyl-aporphines can be prepared as previously described (see, for example, Cannon et al., J. Med. Chem. 31:313 (1988); Hedberg et al., J. Med. Chem. 38:647 (1995); and Granchelli et al., J. Org. Chem. 45:2275 (1980)). R(—)-2-chloro and R(—)-2-bromo aporphines can be prepared using methods analogous to those previously described (see Berenyi et al., Acta Chim. Hung. 120:201 (1985); and Simon et al., Synth. Commun. 21:2309 (1991)). R(—)-2-fluoro-apomorphine (20) and R(—)-2-fluoro-N-n-propylnorapomorphine (22) can be prepared as described in Berenyi et al., J. Chem. Soc. Perkin Trans. I. 2693 (1992); and Berenyi et al., J. Chem. Soc. Perkin Trans. I. 2137 (1993). R(—)-2-fluoro aporphines can be prepared as described in Schemes 2 and 3, below. Any of the above aporphines can be converted to their corresponding esters using the general methods described in Example 14.

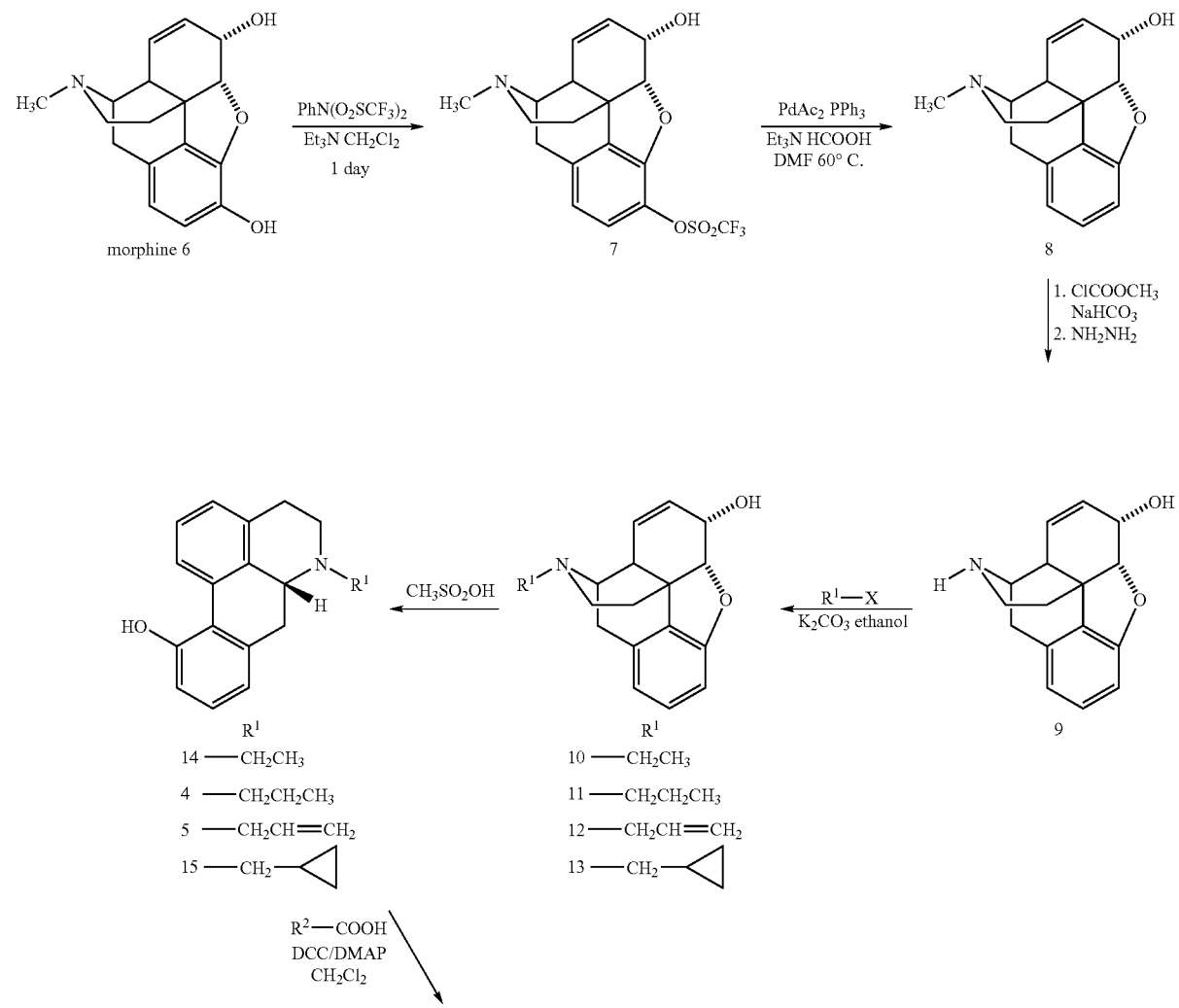

-continued

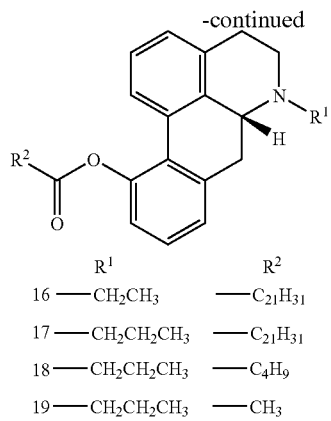

| | R¹ | R² |
|---|---|---|
| 16 | —CH₂CH₃ | —C₂₁H₃₁ |
| 17 | —CH₂CH₂CH₃ | —C₂₁H₃₁ |
| 18 | —CH₂CH₂CH₃ | —C₄H₉ |
| 19 | —CH₂CH₂CH₃ | —CH₃ |

Example 1

Synthesis of 3-O—[(trifluoromethyl)sulfonyl]morphine (compound 7)

A slurry of 5.H₂O (10 g, 32.8 mmol) and Et₃N (7 mL) in anhydrous dichloromethane (500 mL) kept under nitrogen was stirred for 1 h at ambient temperature. N-phenyltrifluoromethanesulfonimide (14 g, 39.4 mmol) was added to the reaction mixture, and after being stirred for 24 hours, it was extracted with 10% aqueous KHCO₃ (3×70 mL). The organic layer was dried on sodium sulfate, filtered, and concentrated in vacuo, to yield a solid product (24.5 g). This solid was dissolved in ether (80 mL), and extracted with 1M HCl (4×120 mL). The pH of the acidic layer was adjusted to 9 by adding ammonium hydroxide, without cooling. After cooling to room temperature the product was extracted with dichloromethane (3×100 mL). The organic layer was washed with brine (100 mL), dried with sodium sulfate, filtered and evaporated, to afford 13.13 g white solid. The solid residue was filtered from a small amount of dry ether, to yield 12.4 g (90%) of pure 7, mp: 122-124° C. (Lit.: 123-124° C.). ¹H and ¹³C NMR spectra were identical with that of the literature data. See Hedberg et al., *J. Med. Chem.* 38:647 (1995).

Example 2

Synthesis of 3-deoxymorphine (compound 8)

Triphenylphosphine (1.2 g, 4.5 mmol) and palladium acetate (0.48 g, 2.03 mmol) were added to a stirred mixture of 7 (10.0 g, 23.98 mmol), triethylamine (15 mL, 106.9 mmol), and formic acid (1.8 mL, 45.1 mmol) in DMF (32 mL) at 40° C., under nitrogen. The mixture was stirred under nitrogen for 5 hours, at 60° C. After cooling to room temperature the reaction mixture was dropwise added to a cooled solution of HCl (30 mL) in water (300 mL). The acidic solution was extracted with dichloromethane (4×100 mL). The pH of the acidic layer was adjusted to 9 by adding ammonium hydroxide with cooling, then it was extracted with dichloromethane (3×100 mL). The organic layer was washed with brine (100 mL), dried with sodium sulfate, filtered and evaporated. The solid residue was filtered from dry ether, washed with ether, to afford 5.7 g (88%) of 8, mp: 224-227° C. (Lit.: 227-229° C.). ¹H and ¹³C NMR spectra were identical to the reported values of the literature data. See Hedberg et al., *J. Med. Chem.* 38:647 (1995).

Example 3

Synthesis of 3-deoxynormorphine (compound 9)

To a stirred mixture of 8 (5.19 g, 19.25 mmol), and NaHCO₃ (26 g) in anhydrous chloroform (270 mL) was slowly added methyl chloroformate (28 mL, 362 mmol) under nitrogen, at 40° C. The temperature was increased to 60° C., and the reaction mixture was stirred over night, filtered, washed with chloroform, and evaporated in vacuo. The oily residue was dissolved in anhydrous methanol (16 mL), and to the stirred methanolic solution hydrazine (31 mL) was added dropwise, under nitrogen. After stirring for 3 days, at 90-100° C., to the reaction mixture water (50 mL) was added with cooling, and extracted with 3:1 (vols) dichloromethane:methanol (5×25 mL). The organic layer was washed with brine (50 mL), dried with sodium sulfate, filtered and evaporated in vacuo. The white solid product was crystallized from anhydrous ether, the crystals were filtered and washed with anhydrous ether, to afford pure 9 (3.71 g, 77%), mp: 216-220° C. ¹H NMR (CDCl₃) δ 1.8-2.0 (2H, m, C—H), 2.6 (1H, m, C—H), 2.8-3.05 (3-H, m, C—H), 2.88 (1-H, s, N—H), 3.67 (1H, m, H-9), 4.19 (1H, m, H-6), 4.82 (1H, d, $J_{5-6}$=8 Hz, H-5), 5.28 (1H, m, H-8), 5.71 (1H, m, H-7), 6.59 (1H, d, $J_{2,3}$=10 Hz, H-3), 6.64 (1H, d, $J_{1,2}$=10 Hz, H-1), 7.02 (1H, t, H-2), MS m/z (rel. intensity) 255 (M, 75%), Anal. (C₁₆H₁₇NO₂) Calcd: C, 75.29; H, 6.67; N, 5.49. Found: C, 75.11; H, 6.70; N, 5.48.

Example 4

General Procedure for the Synthesis of N-alkyl-3-deoxynormorphines (compounds 10-13)

To a stirred mixture of 8 (0.5 g, 1.96 mmol), and NaHCO₃ (0.25 g, 2.98 mmol) in anhydrous ethanol (10 mL) the appropriate alkyl halide (2.5 mmol) was added slowly, under nitrogen. The reaction mixture was allowed to reflux at 80-90° C., for 24 hours. To the reaction mixture water (40 mL) was added, and extracted with ethyl acetate (3×20 mL). The organic layer was washed with brine (20 mL), dried with sodium sulfate, filtered and evaporated in vacuo. The oily crude product was purified by column chromatography (9:1 (vols) chloroform:methanol) to afford pure oils.

Example 5

Characterization of N-ethyl-3-deoxynormorphine (compound 10)

In this case iodoethane was added in higher dose (3 mL, 37.5 mmol).

Yield: 0.4 g (72%), mp (HCl-salt): 241-244° C. $^1$H NMR (from salt, CD$_3$OD) δ 1.4 (3H, t, CH$_3$), 2.0-2.4 (2H, m, C—H), 2.8-3.5 (7H, m, C—H,), 4.2-4.35 (2H, m, H-6, H-9), 4.9 (1H, m, H-5), 5.36 (1H, m, H-8), 5.77 (1H, m, H-7), 6.61 (1H, d, J$_{2,3}$=8 Hz, H-3), 6.69 (1H, m, H-1), 7.07 (1H, t, H-2), MS m/z (rel. intensity) 283 (M, 50%), 268 (M−15, 30%), Anal. (C$_{18}$H$_{21}$NO$_2$HCl) Calcd: C, 67.60; H, 6.88; N, 4.38. Found: C, 67.48; H, 6.91; N, 4.36.

Example 6

Characterization of N-propyl-3-deoxynormorphine (compound 11)

The reaction was carried out with iodopropane. Yield: 0.33 g (57%), mp (HCl-salt): 244-246° C. $^1$H NMR (from the salt, CD$_3$OD) δ 1.07 (3H, t, CH$_3$), 1.77-1.95 (2H, m, C—H), 2.05 (1H, m, C—H), 2.37 (1H, m, C—H), 2.9-3.5 (7H, m, C—H), 3.0 (1H, s, OH), 4.27 (2H, m, H-6, H-9), 4.9 (1H, m, H-5), 5.35 (1H, m, H-8), 5.75 (1H, m, H-7), 6.61 (1H, d, J$_{2,3}$=7 Hz, H-3), 6.69 (1H, d, J$_{1,2}$=7 Hz, H-1), 7.07 (1H, t, H-2), MS m/z (rel. intensity) 297 (M, 20%), 268 (M−29, 95%), Anal. (C$_{19}$H$_{23}$NO$_2$HCl) Calcd: C, 68.36; H, 7.19; N, 4.20. Found: C, 68.18; H, 7.21; N, 4.19.

Example 7

Characterization of N-allyl-3-deoxynormorphine (compound 12)

The reaction was carried out with allyl bromide, and purified by column chromatography (19:1 (vols) chloroform:methanol). Yield: 0.32 g (56%), mp (HCl-salt): 166-168° C. $^1$H NMR (base, CDCl$_3$) δ 1.66 (1H, s, OH), 1.8-1.9 (1H, m, C—H), 2.0-2.12 (1H, m, C—H), 2.27-2.43 (2H, m, C—H), 2.65-2.74 (2H, m, C—H), 3.03 (1H, d, J=20 Hz, H-10β), 3.2 (2H, m, C—H), 3.48 (1H, m, C—H), 4.19 (1H, m, H-6), 4.84 (1H, m, H-5), 5.07-5.32 (3H, m, =C—H), 5.68 (1H, m, H-7), 5.76-5.96 (2H, m, =C—H), 6.58 (1H, d, J=8.5 Hz, H-3), 6.62 (1H, d, J=8.5 Hz, H-1), 7.0 (1H, t, H-2), $^{13}$C NMR (base, CDCl$_3$) δ 21.77, 35.72, 40.86, 42.72, 44.56, 56.27, 58.28, 66.62, 90.68, 106.10, 117.62, 119.0, 128.13, 128.60, 129.76 135.48, 135.71, 158.88. MS m/z (rel. intensity) 295 (M, 100%). Anal. (C$_{19}$H$_{21}$NO$_2$.HCl.H$_2$O) Calcd: C, 65.23; H, 6.91; N, 4.0. Found: C 65.33; H, 6.89; N, 3.99.

Example 8

Characterization of N-cyclopropylmethyl-3-deoxynormorphine (compound 13)

The reaction was carried out with bromomethylcyclopropane. Yield: 0.34 g (57%), mp (HCl-salt): 194-197° C. $^1$H NMR (base, CDCl$_3$) δ 0.16 (2H, m, cyclopropyl C—H), 0.55 (2H, m, cyclopropyl C—H), 0.88 (1H, m, cyclopropyl C—H), 1.64 (1H, s, OH), 1.86 (1H, m, C—H), 2.04-2.16 (1H, m, C—H), 2.28-2.48 (4H, m, C—H), 2.7 (1H, m, C—H), 2.83 (1H, m, C—H), 2.98 (1H, d, J=20 Hz, H-10β), 3.7 (1H, m, C—H), 4.19 (1H, m, H-6), 4.84 (1H, d, H-5), 5.32 (1H, m, H-8), 5.69 (1H, m, H-7), 6.59 (2H, t, H-3, H-1), 7.0 (1H, t, H-2), $^{13}$C NMR (base, CDCl$_3$) δ 3.71, 3.99, 9.35, 21.68, 35.75, 40.89, 42.80, 44.87, 56.21, 59.89, 66.64, 90.75, 106.08, 118.98, 128.10, 128.78, 133.15 135.54, 141.64, 158.89. MS m/z (rel. intensity) 309 (M, 100%). Anal. (C$_{20}$H$_{23}$NO$_2$.HCl) Calcd: C, 69.46; H, 6.66; N, 4.05. Found: C, 69.08; H, 6.71; N, 4.02.

Example 9

General Procedure for the Synthesis of R(—)—N-alkyl-11-hydroxynoraporphines (compounds 14, 4, 5, 15)

The appropriate N-alkyl-3-deoxynormorphine (1.45 mmol) was dissolved in 99% methanesulfonic acid (4 mL, 62 mmol), under nitrogen, at room temperature. The reaction mixture was stirred for 30 minutes, at 90° C., and then after cooling to room temperature there was ice-water (20 mL) added. To the aqueous solution was ammonia added, with cooling to pH=9. The mixture was extracted with dichloromethane (3×20 mL), and the organic layer was washed with brine (20 mL), dried with sodium sulfate and evaporated in vacuo to afford an oily crude product. The crude product was purified by column chromatography (19:1 (vols) chloroform:methanol) to obtain pure oily product, which was converted into the hydrochloride salt with 1 M etheral HCl.

Example 10

Characterization of R(—)—N-ethyl-11-hydroxynoraporphine (compound 14)

From 9 a white solid 13 is obtained (230 mg, 53%), mp: 250'C>dec. $^1$H NMR (CD$_3$OD) δ 1.47 (3H, t, CH$_3$), 2.85 (1H, m, C—H), 3.1-3.5 (5H, m, C—H), 3.77-4.0 (2H, m, C—H), 4.43 (1H, m, C—H), 6.88 (2H, m, H-8, H-10), 7.12 (1H, t, H-9), 7.18 (1H, d, J$_{2,3}$=9 Hz, H-3), 7.37 (1H, t, H-2), 8.4 (1H, d, J$_{1,2}$=9 Hz, H-1), MS m/z (rel. intensity) 265 (M, 60%), Anal. (C$_{18}$H$_{19}$NO.HCl) Calcd: C, 71.64; H, 6.63; N, 4.64. Found: C, 71.58; H, 6.65; N, 4.62.

Example 11

Characterization of R(—)—N-propyl-11-hydroxynoraporphine (compound 4)

From 10, the neutralized reaction mixture was extracted with 3:1 (vols) dichloromethane:methanol (4×20 mL) to yield a white solid (240 mg, 52%), mp: 250'C>dec. (Lit.: 257-258° C.). $^1$H NMR (CD$_3$OD) δ 1.12 (3H, t, CH$_3$), 2.85 (1H, m, C—H), 3.05-3.75 (9H, m, C—H), 3.92 (1H, m, C—H), 6.87 (1H, d, J$_{9,10}$=7.5 Hz, H-10), 6.89 (1H, d, J$_{8,9}$=7.5 Hz, H-8), 7.12 (1H, t, H-9), 7.18 (1H, d, J$_{2,3}$=9 Hz, H-3), 7.36 (1H, t, H-2), 8.39 (1H, d, J$_{1,2}$=9 Hz, H-1), MS m/z (rel. intensity) 279 (M, 80%), Anal. (C$_{19}$H$_{21}$NO.HCl) Calcd: C, 72.25; H, 7.02; N, 4.43. Found: C, 71.98; H, 7.08; N, 4.41.

Example 12

Characterization of R(—)—N-allyl-11-hydroxynoraporphine (compound 5)

From 11, a white solid is obtained (240 mg, 50%), mp: 186-190° C. $^1$H NMR (CD$_3$OD) δ 2.86 (1H, m, C—H), 3.06-3.55 (4H, m, C—H), 3.84-4.02 (2H, m, C—H), 4.3-4.46 (2H, m, C—H), 5.72 (2H, m, =C—H), 6.0-6.18 (1H, m, =C—H), 6.89 (2H, d, J=8.5 Hz, H-8, H-10), 7.12 (1H, t, H-9), 7.18 (1H, d, J=8.2 Hz, H-3), 7.36 (1H, t, H-2), 8.41 (1H, d, J=8.2 Hz, H-1), MS m/z (rel. intensity) 277 (M, 50%), Anal. ($C_{18}H_{17}NO.HCl.H_2O$) Calcd: C, 65.16; H, 6.03; N, 4.22. Found: C, 65.25; H, 6.04; N, 4.23.

Example 13

Characterization of R(—)—N-cyclopropylmethyl-11-hydroxynoraporphine (compound 15)

From 13 the reaction mixture was stirred at 60° C., for 30 minutes. The hydrochloride is a white solid (170 mg, 36%), mp: 195-200° C. (dec.). $^1$H NMR (base, $CDCl_3$) δ 0.2 (2H, m, cyclopropyl C—H), 0.48-0.64 (2H, m, cyclopropyl C—H), 1.0 (1H, m, cyclopropyl C—H), 2.4 (1H, q, C—H), 2.5-2.66 (2H, m, C—H), 2.79 (1H, m, C—H), 2.91-3.26 (3H, m, C—H), 3.4-3.5 (2H, m, C—H), 6.78 (1H, d, J=8.5 Hz, H-8), 6.84 (1H, d, J=8.5 Hz, H-10), 7.06 (2H, t, H-9, H-3), 7.26 (1H, t, H-2), 7.94 (1H, d, J=7.9 Hz, H-1), $^{13}$C NMR (base, $CDCl_3$) δ 2.96, 5.06, 7.44, 29.18, 34.86, 49.12, 59.16, 59.23, 115.55, 120.41, 121.33, 124.31, 126.32, 127.62, 128.03, 131.38, 133.71, 136.13, 138.33, 152.70. MS m/z (rel. intensity) 291 (M, 70%), 290 (M−1, 100%), Anal. ($C_{20}H_{21}NO.HCl$) Calcd: C 73.27; H 6.76; N, 4.27. Found: C, 73.25; H, 6.76; N, 4.25.

Example 14

General Procedure for the Synthesis of R(—)—N-alkyl-11-hydroxyaporphine Esters (compounds 16-19)

The appropriate 11-hydroxy-N-alkylnoraporphine (0.5 mmol), the corresponding acid (0.6 mmol) and a catalytic amount of 4-dimethylaminopyridine (DMAP) were dissolved in anhydrous dichloromethane (20 mL) under nitrogen. To the stirred mixture a solution of N,N-dicyclohexyl-carbodiimide (130 mg, 0.6 mmol) in anhydrous dichloromethane (6 mL) was added at room temperature. After 4 hours stirring at room temperature the reaction mixture was filtered and evaporated to dryness. The crude oily product was purified by means of column chromatography (5:2 (vols) hexane:ethyl acetate) to obtain pure oily product.

Example 15

Characterization of R(—)-11-O-docosahexaenoyl-N-ethyl-noraporphine (compound 16)

Starting from N-ethyl-11-hydroxynoraporphine (14) and cis-4,7,10,13,16,19-docosahexaenoic acid (DHA) the product is a syrupy oil (180 mg, 63%). $^1$H NMR ($CDCl_3$) δ 0.97 (3H, t, $CH_3$), 1.16 (3H, t, $CH_3$), 2.07 (2H, m, C—H), 2.3-2.7 (8H, m, C—H), 2.7-3.0 (10H, s, C—H), 3.0-3.3 (4H, m, C—H), 3.48 (1H, m, C—H) 5.37 (12H, s, =C—H), 7.0 (1H, d, $J_{9,10}$=8 Hz, H-10), 7.07 (1H, d, $J_{8,9}$=8 Hz, H-8), 7.14-7.28 (3H, m, H-2, H-3, H-9), 7.74 (1H, d, $J_{1,2}$=8 Hz, H-1), Anal. ($C_{40}H_{49}NO_2$) Calcd: C, 83.43; H, 8.58; N, 2.43. Found: C, 83.22; H, 8.60; N, 2.43, HPLC: 97.5% purity.

Example 16

Characterization of R(—)-11-O-docosahexaenoyl-N-propyl-noraporphine (compound 17)

Starting from N-propyl-11-hydroxynoraporphine (4) and cis-4,7,10,13,16,19-docosahexaenoic acid (DHA) the product is a syrupy oil (210 mg, 71%). $^1$H NMR ($CDCl_3$) δ 0.97 (6H, t, 2×$CH_3$), 1.58 (2H, m, C—H), 2.07 (2H, m, C—H), 2.35-2.7 (9H, m, C—H), 2.7-3.0 (10H, s, C—H), 3.0-3.2 (3H, m, C—H), 3.41 (1H, d, C—H) 5.37 (12H, s, =C—H), 7.0 (1H, d, $J_{9,10}$=8 Hz, H-10), 7.07 (1H, d, $J_{8,9}$=8 Hz, H-8), 7.14-7.28 (3H, m, H-2, H-3, H-9), 7.72 (1H, d, $J_{1,2}$=8.5 Hz, H-1), Anal. ($C_{41}H_{51}NO_2$) Calcd: C, 83.49; H, 8.71; N, 2.37. Found: C, 83.25; H, 8.74; N, 2.36, HPLC: 99% purity.

Example 17

Characterization of R(—)-11-O-valeryl-N-propyl-noraporphine (compound 18)

Starting from N-propyl-11-hydroxynoraporphine (4) and valeric acid the obtained oily product was converted to the hydrochloride salt with HCl-ether to get white solid product (150 mg, 75%), mp: 232-234° C. (dec.). $^1$H NMR (base, $CDCl_3$) δ 0.95 (6H, m, 2×$CH_3$), 1.25-1.5 (2H, m, C—H), 1.5-2.0 (4H, m, C—H), 2.35-2.65 (5H, m, C—H), 2.75 (1H, d, C—H), 2.9 (1H, m, C—H), 3.05-3.22 (3H, m, C—H), 3.41 (1H, d, J=13, C—H), 7.0 (1H, d, $J_{9,10}$=8 Hz, H-10), 7.07 (1H, d, $J_{8,9}$=7 Hz, H-8), 7.13-7.28 (3H, m, H-2, H-3, H-9), 7.74 (1H, d, $J_{1,2}$=7.5 Hz, H-1), $^{13}$C NMR (base, $CDCl_3$) δ 12.06, 13.69, 19.58, 22.22, 26.70, 29.32, 34.31, 35.03, 48.81, 56.51, 59.17, 122.11, 124.74, 125.85, 125.91, 127.37, 127.64, 128.14, 130.68, 133.64, 135.87, 138.62, 147.31, 171.98, MS m/z (rel. intensity) 363 (M, 60%), HPLC: 99% purity, Anal. ($C_{24}H_{29}NO_2.HCl$) Calcd: C, 72.07; H, 7.56; N, 3.50. Found: C, 71.91; H, 7.58; N, 3.51.

Example 18

Characterization of R(—)-11-O-acetyl-N-propyl-noraporphine (compound 19)

Starting from N-propyl-11-hydroxynoraporphine (3) and glacial acetic acid, the column chromatographic purification was carried out in 19:1 (vols) chloroform:methanol eluent system, and the obtained oily product was converted to the hydrochloride salt with HCl-ether to get white solid product (120 mg, 67%), mp: 250-252° C. (dec.). $^1$H NMR (base, $CDCl_3$) δ 0.96 (3H, t, $CH_3$), 1.5-1.8 (2H, m, C—H), 2.27 (3H, s, $COCH_3$), 2.35-2.65 (3H, m, C—H), 2.75 (1H, m, C—H), 2.9 (1H, m, C—H), 3.05-3.2 (3H, m, C—H), 3.4 (1H, m, C—H), 7.02 (1H, d, $J_{9,10}$=8 Hz, H-10), 7.07 (1H, d, $J_{8,9}$=8 Hz, H-8), 7.16-7.27 (3H, m, H-2, H-3, H-9), 7.75 (1H, d, $J_{1,2}$=7.5 Hz, H-1), $^{13}$C NMR (base, $CDCl_3$) δ 12.06, 19.58, 21.38, 29.34, 35.02, 48.84, 56.52, 59.20, 122.07, 124.54, 125.98, 126.04, 127.33, 127.72, 128.22, 130.69, 133.76, 135.94, 138.68, 147.23, 169.24, MS m/z (rel. intensity) 321 (M, 70%), HPLC: 97% purity, Anal. ($C_{21}H_{23}NO_2.HCl$) Calcd: C, 70.48; H, 6.76; N, 3.91. Found: C, 70.42; H, 6.80; N, 3.89.

Example 19

General Procedure for the Preparation of Starting Materials for the Synthesis of R(—)-2-fluoro-N-alkyl-11-hydroxyaporphines Starting materials for the synthesis of 2-fluoro-N-alkyl-11-hydroxyaporphines can be prepared according to Scheme 2. Starting from thebaine, oxidation with m-chloroperbenzoic acid (see Hauser et al., *J. Med. Chem.* 17:1117 (1974)) led to the formation of 14-hydroxycodeinone, which was then converted to 14-hydroxymorphinone using boron tribromide for the O-demethylation (see Rice, *J. Med. Chem.* 20:164 (1977); Iijima et al., *J. Med. Chem.* 21:398 (1978); and Chiang et al., *J. Am. Chem. Soc.* 100:6195 (1978)). Reduction of the keto group at the 6-position with sodium borohydride yielded 14-hydroxymorphine (see Weiss, *J. Med. Chem.* 8:123 (1965)). Selective removal of the phenolic hydroxyl group at the 3-position via the triflate ester resulted in 14-hydroxy-3-deoxymorphine. The same method was adapted that was previously used in the case of morphine (see Hedberg et al. *J. Med. Chem.* 38:647 (1995)). Reaction with tosyl chloride in the presence of pyridine formed the tosylate ester, which was followed by nucleophile substitution with tetrabutyl ammonium fluoride to produce 6b-fluoro-14-hydroxy-3,6-dideoxymorphine (see Makleit et al., *Acta Chim. Hung.* 74:111 (1972) wherein this method was previously used for the synthesis of 3-methoxy analogs). Treatment with phosphorus tribromide resulted in 7b-bromo-6b-fluoro-3,6-dideoxyneomorphine, which was then converted with sodium tert-butoxide to 6-fluoro-3,6-didemethoxythebaine. N-propyl-3,6-didemethoxynorthebaine was prepared by N-demethylation followed by N-propylation of the N-methyl derivative.

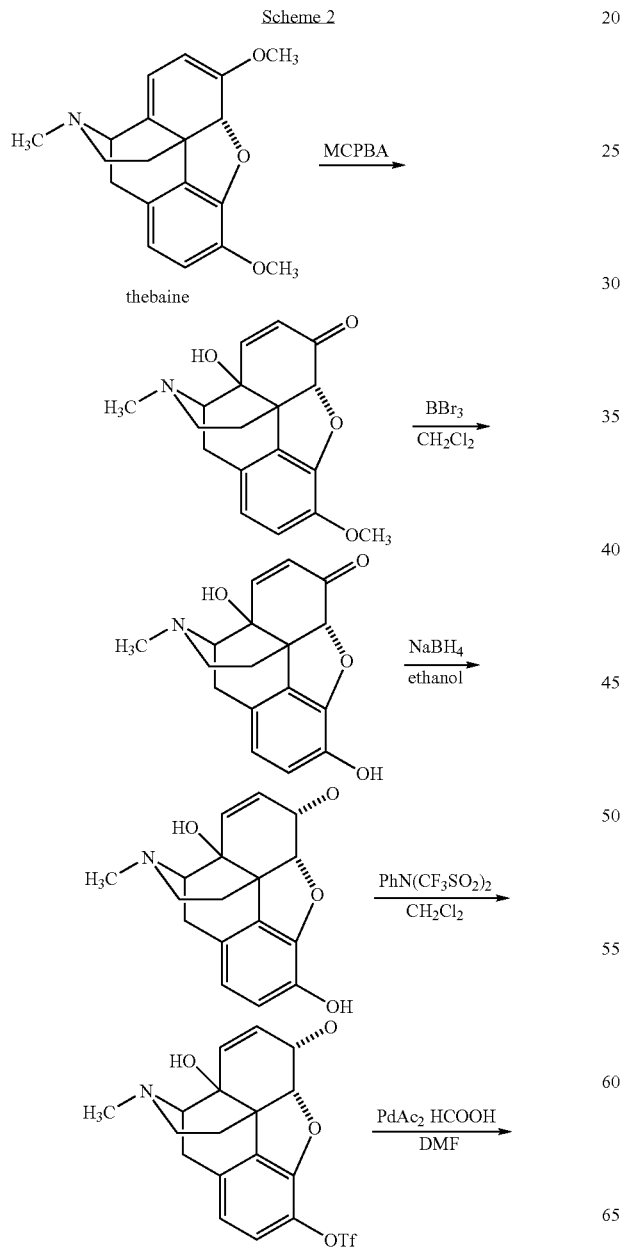

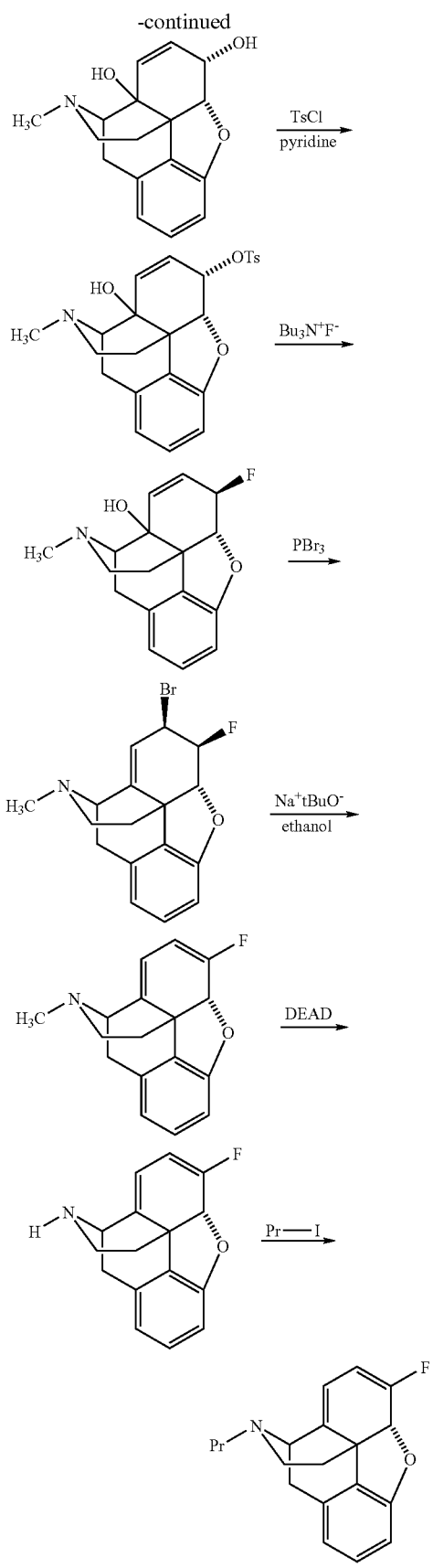

Example 20

General Procedure for the Synthesis of R(—)-2-fluoro-N-alkyl-11-hydroxyaporphines The acid-catalyzed rearrangement of 6-fluoro-3,6-didemethoxythebaine and N-propyl-3,6-didemethoxynorthebaine with methanesulfonic acid led in low yield to the corresponding 2-fluoro-11-hydroxyaporphine (25) and its N-propyl analog (23) due to the formation of side products, such as 2,11-dihydroxyaporphine (24) and the bisaporphine as shown in Scheme 3.

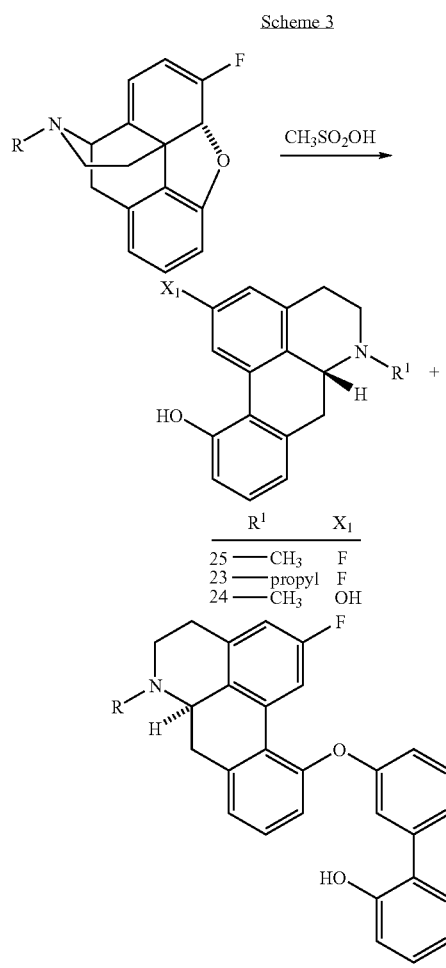

Scheme 3

| | R¹ | X₁ |
|---|---|---|
| 25 | CH₃ | F |
| 23 | propyl | F |
| 24 | CH₃ | OH |

Example 21

Synthesis and Characterization of R(—)-2-fluoro-11-hydroxyaporphine (compound 25)

6-fluoro-3,6-didemethoxythebaine (100 mg, 0.37 mmol) was dissolved in 99% methanesulfonic acid (2 mL), under nitrogen, with ice-cooling. The reaction mixture was placed in a refrigerator for 24 hours. To the reaction mixture was added ice-water (15 mL), followed by ammonia to pH~9. The solution was extracted with ethyl acetate (3×10 mL), the organic layer was washed with brine (15 mL), dried with sodium sulfate, filtered, and evaporated in vacuo. The crude product was purified by column chromatography (Kieselgel 60, 9:1 (vols) ethyl acetate:methanol). The first eluted oily product was 2-fluoro-11-hydroxyaporphine (25 mg, 25%), m.p. (HCl-salt): 250'C>(dec.). $^1$H NMR (base, CD$_3$OD) δ 2.42-2.6 (2H, m, C—H), 2.55 (3H, s, NCH$_3$), 2.76 (1H, m, C—H), 3.03-3.23 (4H, m, C—H), 6.72-6.83 (3H, m, H-3, H-8, H-10), 7.05 (1H, t, H-9), 8.02 (1H, dd, H-1); $^{13}$C NMR (base, CDCl$_3$) δ 29.79, 35.75, 43.89, 53.90, 63.38, 113.69 (d, J=21 Hz), 114.39 (d, J=24 Hz), 116.38, 120.62, 127.63, 129.75, 130.66, 133.47, 135.43, 135.53, 138.80, 156.06 (C-11), 162.79 (d, J=239 Hz, C-2); MS m/z (rel. intensity) 269 (M, 55%). Anal. (C$_{17}$H$_{17}$FClNO) Calcd.: C, 66.78; H, 5.60; N, 4.58. Found: C, 66.81; H, 5.68; N, 4.55.

Example 22

Synthesis and Characterization of R(—)-2-fluoro-N-propyl-11-hydroxynoraporphine (compound 23)

6-fluoro-N-propyl-3,6-didemethoxynorthebaine (80 mg, 0.30 mmol) was dissolved in 99% methanesulfonic acid (2 mL), under nitrogen, with ice-cooling. The reaction mixture was placed in a refrigerator for 22 hours. To the reaction mixture was added ice-water (15 mL), followed by ammonia to pH~9. The solution was extracted with ethyl acetate (3×10 mL), the organic layer was washed with brine (15 mL), dried with sodium sulfate, filtered and evaporated in vacuo. The crude product was purified by column chromatography (silicagel 60, 19:1 (vols) ethyl acetate:methanol). The first eluted oily product was 2-fluoro-N-propyl-11-hydroxynoraporphine (19 mg, 24%), m.p. (HCl-salt): 250° C.>(dec.). $^1$H NMR (base, CDCl$_3$) δ 0.96 (3H, t, CH$_3$), 1.51-1.7 (2H, m, C—H), 2.38-2.63 (3H, m, C—H), 2.73 (1H, m, C—H), 2.91 (1H, m, C—H), 3.05-3.23 (3H, m, C—H), 3.34 (1H, m, C—H), 6.74 (1H, d, J8,9=8 Hz, H-8), 6.77 (1H, dd, H-3), 6.87 (1H, d, J9,10=8 Hz, H-10), 7.08 (1H, t, H-9), 7.8 (1H, dd, H-1); $^{13}$C NMR (base, CDCl$_3$) δ 12.07, 19.41, 29.44, 35.04, 48.84, 56.38, 59.27, 112.34 (d, J=24 Hz, C-1), 113.41 (d, J=21 Hz, C-3), 115.55, 120.72, 128.48, 130.95, 133.34, 133.47, 135.47, 138.71, 152.77 (C-11), 161.26 (d, J=240 Hz, C-2); MS m/z (rel. intensity) 297 (M, 70%). Anal. (C$_{19}$H$_{21}$FClNO) Calcd.: C, 68.36; H, 6.34; N, 4.2. Found: C, 68.31; H, 6.38; N, 4.15.

Example 23

Synthesis and Characterization of R(—)-2,11-dihydroxyaporphine (compound 24)

6-fluoro-3,6-didemethoxythebaine was dissolved in 99% methanesulfonic acid under nitrogen at room temperature with stirring for 24 hours. The solution was worked up and purified as described in Example 21. The reaction yielded about 50% R(—)-2,11-dihydroxyaporphine, 20% R(—)-2-fluoro-11-hydroxyaporphine, and 30% 2-(2'-fluoroaporphine-11'-yl)-11-hydroxyaporphine.

Example 24

In Vitro Affinity Assays

Affinity of N-alkyl R(—)-11-hydroxyaporphines (14, 4, 5, 15, 23, 24) and their esters (17-19) for the dopamine D$_1$ and D$_2$ receptors was determined by radioligand competition assays, using membrane preparations from dopamine-rich corpus striatum (caudatoputamen) tissue from rat forebrain. Adult male Sprague-Dawley rats were sacrificed by decapitation following carbon dioxide narcosis. Brains were quickly removed and dissected on ice. Tissue was homogenized in 50 mM Tris-HCl buffer (pH 7.4) containing 150 mM NaCl, washed twice and resuspended in the same buffer. For the $D_1$ dopamine receptor assay, homogenate was incubated with 0.3 nM [$^3$H]SCH-23390 (Perkin Elmer; Boston, Mass.) for 30 minutes at 30° C. Non-specific binding was defined with 10 μM cis-flupenthixol. See Faedda et al., *Biochem. Pharmacol.* 38:473 (1989). For the $D_2$ receptor assay, homogenate was incubated with 0.075 pM [$^3$H]nemonapride (Perkin Elmer; Boston, Mass.) for 90 minutes at 30° C. Nonspecific binding was defined with 10 μM haloperidol. See Baldessarini et al., *Mol. Pharmacol.* 42:856 (1992). Experiments were carried out in triplicate. Results from the binding experiments are shown below in Table 1.

TABLE 1

Affinity at rat dopamine receptors.

| Compound tested | $D_1$(nM) | $D_2$(nM) |
|---|---|---|
| Apomorphines (comparison standards) | | |
| (1) R(−)-apomorphine (APO) | 214 ± 18 | 13.2 ± 2.1 |
| (20) R(−)-2-F-apomorphine (2-F-APO) | 231 ± 11 | 73.2 ± 11.9 |
| (2) R(−)—N-n-propylnoraporphine (NPA) | 733 ± 74 | 9.87 ± 1.0 |
| (22) R(−)-2-F—N-n-propylnoraporphine (2-F—NPA) | 618 ± 133 | 17.2 ± 1.2 |
| (3) R(−)-11-OH-aporphine | 26.5 ± 1.03 | 108 ± 10.8 |
| N-alkyl R(−)-11-OH-aporphines | | |
| (4) R(−)-11-OH—N-n-propylnoraporphine | 699 ± 118 | 28.5 ± 12.8 |
| (23) R(−)-2-F-11-OH—N-n-propylnoraporphine | 12.6 ± 0.6 | 203 ± 37 |
| (5) R(−)-11-OH—N-allylnoraporphine | 397 ± 51 | 41.1 ± 11.0 |
| (14) R(−)-11-OH—N-ethylnoraporphine | 177 ± 13 | 88.0 ± 15.5 |
| (15) R(−)-11-OH—N-cyclo-propylnoraporphine | 272 ± 18 | 96.3 ± 15.8 |
| (24) R(−)-2,11-diOH-aporphine | 122 ± 8 | 86.0 ± 14.2 |
| Esters of N-propyl-11-hydroxynoraporphine | | |
| (19) R(−)-11-O-acetyl-N-n-propyl-noraporphine | >10,000 | 72.3 ± 6.8 |
| (18) R(−)-11-O-valeryl-N-n-propyl-noraporphine | >20,000 | 340 ± 65 |
| (17) R(−)-11-O-docosahexaenoyl-N-n-propyl-noraporphine | — | — |

Example 25

In Vivo Pharmacology

In vivo potency and oral bioavailability of the aporphine derivatives were determined by measuring stimulation of motor activity in adult male Sprague-Dawley rats using a photobeam activity monitoring system (San Diego Instruments; San Diego, Calif.). See Zhang et al., *Neuropsychopharmacology* 25:624 (2001). The number of animal subjects in each experimental group ranged from 4 to 8. Oral delivery of test agents was achieved using a permanently surgically pre-implanted polyethylene gastric tube to avoid stress associated with conventional oral intubation. For this surgery, rates were anesthetized with 60 mg/kg sodium pentobarbital intraperitoneally. PE50 tubing was inserted and sutured to the stomach, and led subcutaneously to a point of access on the back of the neck, where it was sutured in place. Animals were allowed two weeks to recover prior to behavior testing. The potency of the aporphine compounds was expressed as the sum of behavioral scores at each time of rating until locomotor responses returned to their pre-injection baseline levels, and relative to that (standard score=1) produced by intraperitoneal injection of 4 μmol/kg R(—)-apomorphine, the effects of which lasted for one hour. In addition to the activity sum-score, duration of action is also provided Table 2.

TABLE 2

Induced motor activation.

| Compound tested | (μmol/kg) | Route | Response[1] | Duration hours |
|---|---|---|---|---|
| Apomorphines (comparison standards) | | | | |
| (1) R(−)-apomorphine | 4 | peritoneal | 1 | 1 |
| | 4 | gastric | 0 | — |
| | 20 | gastric | 0 | — |
| (2) R(−)-N-n-propylnoraporphine (NPA) | 4 | peritoneal | 12 | 8 |
| | 4 | gastric | 0 | — |
| | 20 | gastric | 68 | 14 |
| N-alkyl R(−)-11-OH-aporphines | | | | |
| (4) R(−)-11-OH—N-n-propylnoraporphine | 4 | peritoneal | 24 | 8 |
| | 4 | gastric | 0 | — |
| | 20 | gastric | 76 | 18 |
| (14) R(−)-11-OH—N-ethylnoraporphine | 4 | peritoneal | 12 | 4 |
| | 4 | gastric | 0 | — |
| | 20 | gastric | 0 | — |
| Esters of N-propyl-11-hydroxynoraporphine | | | | |
| (19) R(−)-11-O-acetyl-N-n-propyl-noraporphine | 4 | peritoneal | 12 | 8 |
| | 4 | gastric | 0 | — |
| | 20 | gastric | 168 | 16 |

TABLE 2-continued

Induced motor activation.

| Compound tested | (μmol/kg) | Route | Response[1] | Duration hours |
|---|---|---|---|---|
| (18) R(−)-11-O-valeryl-N-n-propyl-noraporphine | 4 | peritoneal | 53 | 12 |
|  | 4 | gastric | 0 | — |
|  | 20 | gastric | 99 | 14 |
| (17) R(−)-11-O-docosahexaenoyl-N-n-propyl-noraporphine | 4 | cutaneous | 0 | — |
|  | 4 | gastric | 0 | — |
|  | 20 | cutaneous | 5 | 6 |
|  | 20 | gastric | 75 | 12 |

[1]Response = total of electronically monitored locomotor responses, scored over time.

Example 26

In Vitro Affinity at Human Receptors in Transfected Cell Membranes

Affinity data were obtained in cells transfected with human D1, D2, or D3 receptor cDNA. Cells were grown and harvested using standard procedures. Assays were performed using tritium-labeled ligands: SCH-23390 for D1, nemonapride for D2, and 7-OH-DPAT for D3. Results of this assay are provided below in Table 3.

TABLE 3

Affinity at human receptors.

| Compound tested | $D_1$(nM) | $D_2$(nM) | $D_3$(nM) |
|---|---|---|---|
| (2) R(−)—N-n-propylnoraporphine | 803 ± 135 | 28.7 ± 2.4 | 0.51 ± 0.07 |
| (22) R(−)-2-F—N-n-propylnoraporphine | 414 ± 30.0 | 46.0 ± 2.6 | 2.49 ± 0.18 |
| (1) R(−)-apomorphine | 548 ± 31.0 | 99.6 ± 9.6 | 41.5 ± 8.6 |
| (5) R(−)-11-OH—N-allylnoraporphine | 944 ± 149 | 113 ± 17.0 | 3.95 ± 0.49 |
| (4) R(−)-11-OH—N-n-propylnoraporphine | 1282 ± 209 | 177 ± 17.0 | 4.89 ± 1.06 |
| (14) R(−)-11-OH—N-ethylnoraporphine | 362 ± 38.0 | 283 ± 53.0 | 36.7 ± 4.0 |
| (15) R(−)-11-OH—N-cyclo-propylnoraporphine | — | 436 ± 39.0 | 30.1 ± 3.5 |

Example 27

Rat Model of Hemiparkinsonism

Selective lesions of the nigrostrial DA pathway with the neurotoxin 6-hydroxydopamine (OHDA) results in slowly evolving denervation supersensitivity of postsynaptic DA receptors in neostriatum that is believed to mimic conditions found in clinical Parkinson's Disease. When adult rats with unilateral 6-OHDA lesions are challenged with drugs that interact with DA neurotransmission, rotational behavior occurs. Indirect DA agonists, such as methylphenidate and amphetamine, that block the neuronal reuptake, induce ipsilateral rotation toward the lesioned side, whereas direct receptor agonists, such as R(—)-apomorphine, induce rotation contralateral to the lesion (U. Ungerstadt, *Acta Physiol. Scand.* 82:51 (1971); and U. Ungerstadt, *Acta Physiol. Scand.* 82:69 (1971)).

These robust and quantifiable behavioral responses are believed to reflect laterally biased DA transmission caused by DA overflow in the intact side induced by indirect agonists and stimulation of supersensitized postsynaptic DA receptors in the lesioned side by direct agonists.

Unilateral 6-OHDA lesioning of the nigrostriatal DA pathway is carried out as detailed previously (see Creese et al., *Science* 197:596 (1977); and Zhang et al., *Pharmacol. Biochem. Behav.* 69:111 (2001)). Adult male Sprague-Dawley rats initially weighing 220 to 250 grams are maintained individually under a 12 hour artificial light/dark schedule (on, 07:00-19:00 h) with free access to standard rat chow and tap water. Rats are pretreated with the monoamine oxidase inhibitor pargyline hydrochloride (30 mg/kg, i.p., to potentiate the toxic amine) 60 minutes prior to microinfusion of 6-OHDA hydrobromide under anesthesia produced by sodium pentobarbital (60 mg/kg, i.p.). The neurotoxin (equivalent to 20 μg free base in 2 μl of 0.9% (w/v) saline containing 1 mM ascorbic acid) is injected to substantia nigra compacta over 2 minutes using a stereotaxic holder, with an additional 5 minutes allowed for equilibration of toxin in tissue. The stereotactic coordinates are: A–P=−5.8, D-V=8.0, L=2.0 mm, with the incisor bar set at 3.0 mm below zero. Rats are allowed 2 weeks to recover from the surgery before behavioral testing.

Rotational behavior is monitored visually in a clear Plexiglas hemispherical chamber (21 cm radius) by an experienced observer between 10:00 h and 16:00 h to minimize variance due to circadian rhythms. Subjects are initially screened for rotational behavior with an acute challenge with R(—)-apomorphine (0.5 mg/kg, i.p.). Rats displaying robust and consistent contralateral rotations are used further to test novel agents. The number of complete (360°) rotations is accumulated for 30 minutes after rotation begins. Rats are decapitated 72 hours after testing for histological verification of lesions, using autoradiographic analysis with [$^3$H]β-CIT, an improved radioligand to label the DA transporter (DAT) protein (see Kula et al., *Eur. J. Pharmacol.* 331:333 (1997); and Zhang et al., *Neuropsychopharmacology,* 25:624 (2001)). The results are provided in FIGS. 1A-1F for compounds 2, 4, and 19. Rotational behavior (turns per unit time) is an indicator of an agent's effectiveness for treating Parkinson's disease.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound selected from R(−)-10-methyl-11-O-acetyl-N-n-propyl-noraporphine, R(−)-10-methyl-11-O-propionyl-N-n-propyl-noraporphine, R(−)-10-methyl-11-O-isobutyryl-N-n-propyl-noraporphine, R(−)-10-methyl-11-O-butyryl-N-n-propyl-noraporphine, R(−)-10-methyl-11-O-isovaleryl-N-n-propyl-noraporphine, R(−)-10-methyl-11-O-valeryl-N-n-propyl-noraporphine, and pharmaceutically acceptable salts thereof.

2. A compound selected from R(−)-10-methoxy-11-O-propionyl-N-n-propyl-noraporphine, R(−)-10-methoxy-11-O-isobutyryl-N-n-propyl-noraporphine, R(−)-10-methoxy-11-O-butyryl-N-n-propyl-noraporphine, R(−)-10-methoxy-11-O-isovaleryl-N-n-propyl-noraporphine, R(−)-10-methoxy-11-O-valeryl-N-n-propyl-noraporphine, and pharmaceutically acceptable salts thereof.

3. A compound selected from R(−)-2-fluoro-11-O-acetyl-N-n-propyl-noraporphine, R(−)-2-fluoro-11-O-propionyl-N-n-propyl-noraporphine, R(−)-2-fluoro-11-O-isobutyryl-N-n-propyl-noraporphine, R(−)-2-fluoro-11-O-butyryl-N-n-propyl-noraporphine, R(−)-2-fluoro-11-O-isovaleryl-N-n-propyl-noraporphine, R(−)-2-fluoro-11-O-valeryl-N-n-propyl-noraporphine, and pharmaceutically acceptable salts thereof.

4. A compound of formula III:

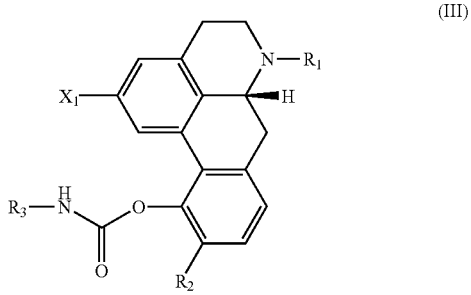

(III)

or a pharmaceutically acceptable salt thereof,
wherein
$X_1$ is H, F, Cl, Br, I, OH, or $OCH_3$;
$R_1$ is $CH_3$, $CH_2CH_3$, $CH_2CH_2CH_3$, $CH_2CH_2{=}CH_2$, or cyclopropylmethyl;
$R_2$ is H, $CH_3$, or $OCH_3$; and
$R_3$ is H, methyl, ethyl, n-propyl, isopropyl, cyclopropyl, cyclopropylmethyl, cyclopropylethyl, n-butyl, iso-butyl, sec-butyl, tert-butyl, vinyl, allyl, 2-cyclopropyl-1-ethenyl, 1-propenyl, 1-butenyl, 2-butenyl, 3-butenyl, 2-methyl-1-propenyl, 2-methyl-2-propenyl, ethynyl, 1-propynyl, 2-propynyl, 1-butynyl, 2-butynyl, or 3-butynyl.

5. The compound of claim 4, wherein said compound is R(−)-11-O-methylcarbamoyl-N-n-propyl-noraporphine, R(−)-11-O-ethylcarbamoyl-N-n-propyl-noraporphine, R(−)-11-O-isopropylcarbamoyl-N-n-propyl-noraporphine, R(−)-11-O-n-propylcarbamoyl-N-n-propyl-noraporphine, R(−)-11-O-isobutylcarbamoyl-N-n-propyl-noraporphine, or R(−)-11-O-n-butylcarbamoyl-N-n-propyl-noraporphine.

6. The compound of claim 4, wherein said compound is R(−)-10-methyl-11-O-methylcarbamoyl-N-n-propyl-noraporphine, R(−)-10-methyl-11-O-ethylcarbamoyl-N-n-propyl-noraporphine, R(−)-10-methyl-11-O-isopropylcarbamoyl-N-n-propyl-noraporphine, R(−)-10-methyl-11-O-n-propylcarbamoyl-N-n-propyl-noraporphine, R(−)-10-methyl-11-O-isobutylcarbamoyl-N-n-propyl-noraporphine, or R(−)-10-methyl-11-O-n-butylcarbamoyl-N-n-propyl-noraporphine.

7. The compound of claim 4, wherein said compound is R(−)-10-methoxy-11-O-methylcarbamoyl-N-n-propyl-noraporphine, R(−)-10-methoxy-11-O-ethylcarbamoyl-N-n-propyl-noraporphine, R(−)-10-methoxy-11-O-isopropylcarbamoyl-N-n-propyl-noraporphine, R(−)-10-methoxy-11-O-n-propylcarbamoyl-N-n-propyl noraporphine, R(−)-10-methoxy-11-O-isobutylcarbamoyl-N-n-propyl-noraporphine, or R(−)-10-methoxy-11-O-n-butylcarbamoyl-N-n-propyl-noraporphine.

8. The compound of claim 4, wherein said compound is R(−)-2-fluoro-11-O-methylcarbamoyl-N-n-propyl-noraporphine, R(−)-2-fluoro-11-O-ethylcarbamoyl-N-n-propyl-noraporphine, R(−)-2-fluoro-11-O-isopropylcarbamoyl-N-n-propyl-noraporphine, R(−)-2-fluoro-11-O-n-propylcarbamoyl-N-n-propyl-noraporphine, R(−)-2-fluoro-11-O-isobutylcarbamoyl-N-n-propyl-noraporphine, or R(−)-2-fluoro-11-O-n-butylcarbamoyl-N-n-propyl-noraporphine.

9. A method of treating Parkinson's disease in a mammal, said method comprising administering to said mammal an effective amount of a compound of any one of claims 1-4.

10. A method of treating sexual dysfunction in a mammal, said method comprising administering to said mammal an effective amount of a compound of any one of claims 1-4.

11. The method of claim 9 or 10, wherein said compound is administered orally.

12. The method of claim 9 or 10, wherein said compound is administered intravenously.

13. The method of claim 9 or 10, wherein said compound is administered subcutaneously.

14. The method of claim 9 or 10, further comprising the administration of an effective amount of an anti-emetic agent.

15. The method of claim 14 wherein said anti-emetic agent is nicotine, lobeline sulfate, pipamazine, oxypendyl hydrochloride, ondansetron, buclizine hydrochloride, cyclizine hydrochloride, dimenhydrinate, scopolamine, metopimazine, benzauinamine hydrochloride or diphenidol hydrochloride.

16. The compound R(−)-10-methoxy-11-O-acetyl-N-n-propyl-noraporphine.

17. A pharmaceutical composition comprising a compound selected from R(−)-10-methyl-11-O-acetyl-N-n-propyl-noraporphine, R(−)-10-methyl-11-O-propionyl-N-n-propyl-noraporphine, R(−)-10-methyl-11-O-isobutyryl-N-n-propyl-noraporphine, R(−)-10-methyl-11-O-butylyl-N-n-propyl-noraporphine, R(−)-10-methyl-11-O-isovaleryl-N-n-propyl-noraporphine, R(−)-10-methyl-11-O-valeryl-N-n-propyl-noraporphine, and pharmaceutically acceptable salts thereof, and a pharmaceutically acceptable excipient.

18. A pharmaceutical composition comprising a compound selected from R(−)-10-methoxy-11-O-propionyl-N-n-propyl-noraporphine, R(−)-10-methoxy-11-O-isobutyryl-N-n-propyl-noraporphine, R(−)-10-methoxy-11-O-butyryl-N-n-propyl-noraporphine, R(−)-10-methoxy-11-O-isovaleryl-N-n-propyl-noraporphine, R(−)-10-methoxy-11-O-valeryl-N-n-propyl-noraporphine, and pharmaceutically acceptable salts thereof, and a pharmaceutically acceptable excipient.

19. A pharmaceutical composition comprising a compound of formula III:

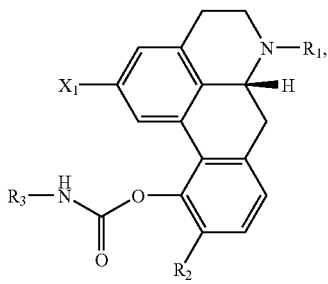

or a pharmaceutically acceptable salt thereof, wherein
$X_1$ is H, F, Cl, Br, I, OH, or $OCH_3$;
$R_1$ is $CH_3$, $CH_2CH_3$, $CH_2CH_2CH_3$, $CH_9CH_9{=}CH_2$, or cyclopropylmethyl;
$R_2$ is H, $CH_3$, or $OCH_3$; and
$R_3$ is H, methyl, ethyl, n-propyl, isopropyl, cyclopropyl, cyclopropylmethyl, cyclopropylethyl, n-butyl, iso-butyl, sec-butyl, tert-butyl, vinyl, allyl, 2-cyclopropyl-1-ethenyl, 1-propenyl, 1-butenyl, 2-butenyl, 3-butenyl, 2-methyl-1-propenyl, 2-methyl-2-propenyl, ethynyl, 1-propynyl, 2-propynyl, 1-butynyl, 2-butynyl, or 3-butynyl; and
a pharmaceutically acceptable excipient.

20. The pharmaceutical composition of claim 19, wherein said compound is selected from R(−)-11-O-methylcarbamoyl-N-n-propyl noraporphine, R(−)-11-O-ethylcarbamoyl-N-n-propyl-noraporphine, R(−)-11-O-isopropylcarbamoyl-N-n-propyl-noraporphine, R(−)-11-O-n-propylcarbamoyl-N-n-propyl-noraporphine, R(−)-11-O-isobutylcarbamoyl-N-n-propyl-noraporphine, R(−)-11-O-n-butylcarbamoyl-N-n-propyl-noraporphine, and pharmaceutically acceptable salts thereof.

21. The pharmaceutical composition of claim 19, wherein said compound is selected from R(−)-10-methyl-11-O-methylcarbamoyl-N-n-propyl-noraporphine, R(−)-10-methyl-11-O-ethylcarbamoyl-N-n-propyl-noraporphine, R(−)-10-methyl-11-O-isopropylcarbamoyl-N-n-propyl-noraporphine, R(−)-10-methyl-11-O-n-propylcarbamoyl-N-n-propyl-noraporphine, R(−)-10-methyl-11-O-isobutylcarbamoyl-N-n-propyl-noraporphine, R(−)-10-methyl-11-O-n-butylcarbamoyl-N-n-propyl-noraporphine, and pharmaceutically acceptable salts thereof.

22. The pharmaceutical composition of claim 19, wherein said compound is selected from R(−)-10-methoxy-11-O-methylcarbamoyl-N-n-propyl-noraporphine, R(−)-10-methoxy-11-O-ethylcarbamoyl-N-n-propyl-noraporphine, R(−)-10-methoxy-11-O-isopropylcarbamoyl-N-n-propyl-noraporphine, R(−)-10-methoxy-11-O-n-propylcarbamoyl-N-n-propyl-noraporphine, R(−)-10-methoxy-11-O-isobutylcarbamoyl-N-n-propyl-noraporphine, R(−)-10-methoxy-11-O-n-butylcarbamoyl-N-n-propyl-noraporphine, and pharmaceutically acceptable salts thereof.

23. The pharmaceutical composition of claim 19, wherein said compound is selected from R(−)-2-fluoro-11-O-methylcarbamoyl-N-n-propyl-noraporphine, R(−)-2-fluoro-11-O-ethylcarbamoyl-N-n-propyl-noraporphine, R(−)-2-fluoro-11-O-isopropylcarbamoyl-N-n-propyl-noraporphine, R(−)-2-fluoro-11-O-n-propylcarbamoyl-N-n-propyl-noraporphine, R(−)-2-fluoro-11-O-isobutylcarbamoyl-N-n-propyl-noraporphine, R(−)-2-fluoro-11-O-n-butylcarbamoyl-N-n-propyl-noraporphine, and pharmaceutically acceptable salts thereof.

24. A pharmaceutical composition comprising R(−)-10-methoxy-11-O-acetyl-N-n-propyl-noraporphine, or a pharmaceutically acceptable salt thereof and a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,648,995 B2 | Page 1 of 2 |
| APPLICATION NO. | : 11/105024 | |
| DATED | : January 19, 2010 | |
| INVENTOR(S) | : Neumeyer et al. | |

It is certified that error appears in the above-identified patent and that said Letters Patent is hereby corrected as shown below:

Title Page 2, Item (56), Right column, in the Scatton and Worms entry, replace "Striatel" with --Striatal--.

Column 3, Line 10, replace "10-O-methyl" with --10-methyl--.

Column 6, Line 39, replace "depressions" with --depression)--.

Column 9, Lines 5-6, replace "hydroxyalkyl, hydroxyalkyl," with --hydroxyalkyl,--;

Line 20, replace "$C_{6-2}$" with --$C_{6-12}$--.

Column 11, Line 39, replace "A. R. Gennaro A R." with --A. R. Gennaro--.

Column 12, Line 3, replace "sulfuric acid" with --sulfuric acid,--.

Column 18, Line 33, replace "250'" with --250°--;

Line 49, replace "250'" with --250°--.

Column 19, Line 35, replace "N, N" with --N, N'--.

Signed and Sealed this
Nineteenth Day of June, 2012

David J. Kappos
*Director of the United States Patent and Trademark Office*

Column 21, Line 49, 4th compound of Scheme 2, replace with new compound below.
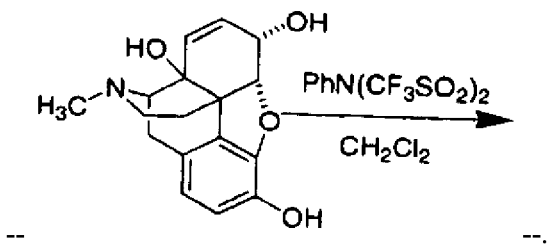
Line 58, 5th compound of Scheme 2, top right, replace with new compound below.
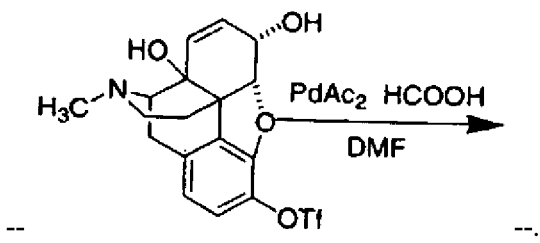
Column 24, Line 2, replace "250'" with --250°--.
Column 27, Line 51, replace "nigrostrial" with --nigrostriatal--.
Column 31, Line 20, replace "CH$_9$CH$_9$" with --CH$_2$CH$_2$--.